(12) United States Patent
Yount et al.

(10) Patent No.: US 12,037,368 B2
(45) Date of Patent: Jul. 16, 2024

(54) ANTIMICROBIAL TYPE-II BACTERIOCINS

(71) Applicant: Lundquist Institute for Biomedical Innovation at Harbor-UCLA Medical Center, Torrance, CA (US)

(72) Inventors: Nannette Y. Yount, San Juan Capistrano, CA (US); Michael R. Yeaman, Redondo Beach, CA (US)

(73) Assignee: Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 184 days.

(21) Appl. No.: 17/468,311

(22) Filed: Sep. 7, 2021

(65) Prior Publication Data

US 2021/0403512 A1 Dec. 30, 2021

Related U.S. Application Data

(63) Continuation of application No. 16/612,245, filed as application No. PCT/US2018/032136 on May 10, 2018, now Pat. No. 11,124,547.

(60) Provisional application No. 62/505,015, filed on May 11, 2017.

(51) Int. Cl.
| | |
|---|---|
| *C07K 14/32* | (2006.01) |
| *A61K 38/16* | (2006.01) |
| *A61K 45/06* | (2006.01) |
| *C07K 14/195* | (2006.01) |
| *C07K 14/325* | (2006.01) |
| *G16B 30/10* | (2019.01) |

(52) U.S. Cl.
CPC ............ *C07K 14/32* (2013.01); *A61K 38/164* (2013.01); *A61K 45/06* (2013.01); *C07K 14/195* (2013.01); *C07K 14/325* (2013.01); *G16B 30/10* (2019.02)

(58) Field of Classification Search
CPC .... C07K 14/32; C07K 14/195; C07K 14/325; A61K 38/164; A61K 45/06; A61K 38/14; A61K 38/00; G16B 30/10; G01N 33/50; G06F 7/00
See application file for complete search history.

(56) References Cited

U.S. PATENT DOCUMENTS

| | | | |
|---|---|---|---|
| 6,416,779 B1 * | 7/2002 | D'Augustine | A61P 15/00 424/431 |
| 8,389,679 B2 | 3/2013 | Eckert et al. | |
| 9,326,523 B2 * | 5/2016 | van der Donk | A61K 38/00 |
| 11,124,547 B2 * | 9/2021 | Yount | G01N 33/50 |
| 2010/0129864 A1 | 5/2010 | Stiles et al. | |
| 2011/0039761 A1 | 2/2011 | Eckert et al. | |

OTHER PUBLICATIONS

Acuña et al., "A new hybrid bacteriocin, Ent35-MccV, displays antimicrobial activity against pathogenic Gram-positive and Gram-negative bacteria", FEBS Open Bio., 2012, vol. 2, pp. 12-19.
Challacombe et al., "Genome Announcement: The Complete Genome Sequence of Baciullus thurigiensis Al Hakam", Journal of Bacteriology, May 2007, pp. 3680-3681.
GenBank-AEW58258, Hypothetical protein bcf_25825 [Bacillus cereus F837/76] GenBank Accession No. AEW58258, Jan. 30, 2014, retrieved on Jun. 28, 2018, from the Internet: URL:https://www.ncbi.nim.nih.gov/protein/AEW58258/1?report=genbank&log$=prottop&blast_rank=1&RID=KANPXPVW015.
International Search Report and Written Opinion for PCT/US2018/032136 dated Sep. 10, 2018, 15 pages.
Yang et al. "Antibacterial activities of bacteriocins: application in foods and pharmaceuticals", Front Microbiol., 2014, vol. 5:241, pp. 1-10.

* cited by examiner

*Primary Examiner* — Marcela M Cordero Garcia
(74) *Attorney, Agent, or Firm* — Sheppard Mullin Richter & Hampton LLP

(57) ABSTRACT

Computational systems and methods are described for identifying new type-II bacteriocins using a systemic consensus formula and other related criteria. Newly identified type-II bacteriocin peptides are tested experimentally and show potent microbiocidal activities.

4 Claims, 6 Drawing Sheets

Specification includes a Sequence Listing.

ANTIMICROBIAL TYPE-II BACTERIOCINS

CROSS REFERENCE TO RELATED APPLICATIONS

This application is a continuation of U.S. Application Ser. No. 16/612,245, filed Nov. 8, 2019, which is the U.S. national stage application of International Application No. PCT/US2018/032136, filed May 10, 2018, which claims the benefit under 35 U.S.C. § 119(e) of U.S. Provisional Application No. 62/505,015, filed May 11, 2017, the contents of which are incorporated by reference in their entirety into the present disclosure.

SEQUENCE LISTING

The instant application contains a Sequence Listing which has been submitted in ASCII format via EFS-Web and is hereby incorporated by reference in its entirety. Said ASCII copy, created on May 10, 2018, is named 254303WO_ST25.txt and is 608,015 bytes in size.

BACKGROUND

One of the most ancient arms of organismal host defense first arose in prokaryotes as a means to neutralize their competitors. This host defense armamentarium is likely more vast than the known microbial kingdom and is comprised of both ribosomally and non-ribosomally synthesized compounds. Of the ribosomally-synthesized compounds one of the most well characterized groups are the Class II bacteriocins which are synthesized primarily by Gram-positive organisms.

The majority of Class II bacteriocins are initially synthesized as precursors containing a relatively well conserved signal peptide domain. One characteristic feature of this domain, is the presence of a double-glycine motif which occurs just upstream of the signal peptide cleavage site. Processing of the signal peptide has been shown to be carried out by a class of dedicated membrane-bound ABC transporters which are conserved across many bacteriocin-expressing bacterial species.

SUMMARY

It is contemplated that since Class II bacteriocins are processed via a common enzymatic process, most bacteriocin signal peptides contain elements that are conserved with a high degree of fidelity across many family members. As shown in the examples, an analysis of these conserved elements led to the creation of a consensus formula that was representative of a majority of the known class II bacteriocin families. This consensus formula was used a primary screen for previously uncharacterized class II bacteriocin families in online protein databases.

In addition to this conserved consensus, many class II bacteriocins were predicted, and/or shown, to form amphipathic helices when interacting with hydrophobic environments that mimic the microbial plasma membrane. Such amphipathic helices are common to many classes of antimicrobial peptides and are important for their membrane permeabilizing activities. With this discovery, as a means to selectively enrich for antimicrobial compounds, a new amphipathic pattern-search component is disclosed as a component of the search method.

This multi-component search method of the present technology recovered a large number of the known class II bacteriocins from a broad spectrum of organisms. Moreover, the method identified many putative bacteriocin sequences, some from organisms for which no bacteriocin peptides have been identified to date. A number of these putative bacteriocins were synthesized and found to have potent microbicidal activity against a broad spectrum of prototypic Gram-positive, Gram-negative and fungal organisms.

One embodiment of the present disclosure provides a peptide comprising an amino acid sequence selected from the group consisting of FKVIVTDAGHY-PREWGKQLGKWIGSKIK (SEQ ID NO: 5), KRNYSIEKYVKNY1DFIKKAIDIFRPMPI (SEQ ID NO: 6), KTIATNATYYPNKWAKSAGKWIASKIK (SEQ ID NO: 7), QYDKTGYKIGKTVGTIVRKGFEIWSIFK (SEQ ID NO: 8), and an amino acid derived from SEQ ID NO: 5, 6, 7 or 8 with one amino acid substitution, wherein the peptide is not longer than 45 amino acid residues in length.

In some embodiments, the peptide has antimicrobial activity. In some embodiments, the peptide comprises the amino acid sequence of SEQ ID NO: 5, 6, 7, or 8.

In some embodiments, the peptide is not longer than 40 amino acid residues in length. In some embodiments, the peptide is not longer than 35 amino acid residues in length.

Also provided, in one embodiment, is a peptide comprising an amino acid sequence of Table 2 or 3 or SEQ ID NO: 328-1884 or an amino acid derived from a sequence of Table 2 or 3 or SEQ ID NO:328-1884 with one amino acid substitution, wherein the peptide is not longer than 45 amino acid residues in length.

In some embodiments, the peptide includes one or more non-natural amino acid residue.

Also provided, in one embodiment, is a composition comprising the peptide and a pharmaceutically acceptable carrier. In some embodiments, the composition further comprises an antimicrobial agent. In some embodiments, the antimicrobial agent is selected from the group consisting of imipenem, ceftazidime, colistin, chloroquine, artemisinin, vancomycin and daptomycin.

Also provided, in one embodiment, is a method of treating an infection in a patient in need thereof, comprising administering to the patient an effective amount of a peptide comprising an amino acid sequence of Table 2 or 3 or SEQ ID NO:328-1884 or an amino acid derived from a sequence of Table 2 or 3 or SEQ ID NO:328-1884 with one amino acid substitution. In some embodiments, the infection is caused by a Gram-negative bacterium, a Gram-positive bacterium or a fungus.

Yet another embodiment provides a computer-implemented method of identifying a type-II bacteriocin, comprising: searching in a protein database, with one or more processors, for proteins comprising a fragment matching a first consensus formula for type-II bacteriocin; filtering the searched proteins to remove proteins that do not contain an alpha-helical domain; calculating a score for the fragment in each of the searched proteins for one or more parameters selected from hydrophobic moment, mean hydrophobicity, net charge, frequencies or ratio of K and R, or isoelectric point; and identifying a type-II bacteriocin based on the scores.

In some embodiments, the first consensus formula comprises [LI]-[KREDNQSTYH]-X-[KREDNQSTYH]-X-[MLV]-X-X-[IVLT]-X-G-G, wherein X denotes any amino acid.

In some embodiments, the method further comprises searching in the protein database for proteins that match a hidden Markov Model built for type-II bacteriocin.

In some embodiments, the alpha-helical domain is identified with a second consensus formula comprising X-[VILMCFWYAG]-[KRHEDNQSTAG]-[KRHEDNQSTAG]-[VILMCFWYAG]-[VILMCFWYAG]-[KRHEDNQSTAG]-[KRHEDNQSTAG]-[VILMCFWYAG]-X-[KRHEDNQSTAG]-[VILMCFWYAG], wherein X denotes any amino acid residue.

In some embodiments, the parameters comprise hydrophobic moment and isoelectric point. In some embodiments, the search results are limited to proteins that are 80 amino acid residues or fewer in length and containing the fragment within the first 25 amino acid residues.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the technology are utilized, and the accompanying drawings of which:

DETAILED DESCRIPTION

Figure 1:
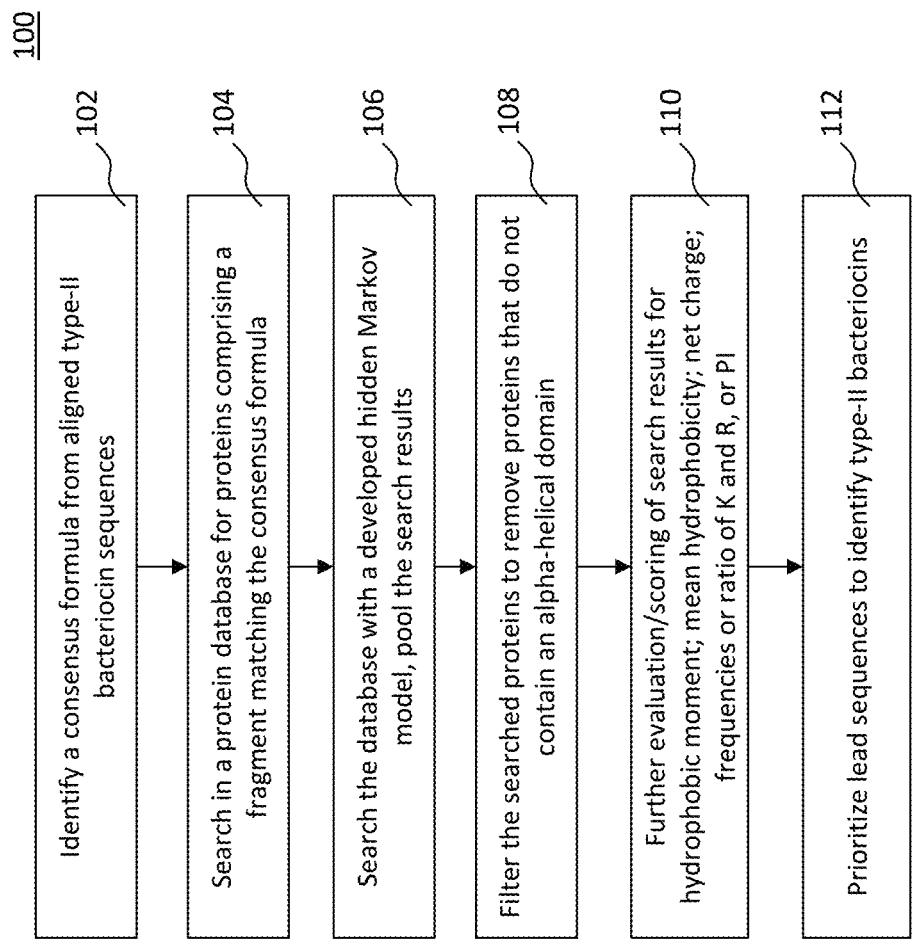
FIG. 1 illustrates an example process flow chart of a method, according to some implementations.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

1. Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure.

Likewise, the present disclosure also includes sequences that have one, two, three, four, or five substitution, deletion or addition of amino acid residues or nucleotides as compared to the reference sequences.

In any of the embodiments described herein, analogs of a peptide comprising any amino acid sequence described herein are also provided, which have at least about 80%, or at least about 83%, or at least about 85%, or at least about 90%, or at least about 95%, or at least about 98%, or at least about 99% sequence identity to any of reference amino acid sequences. In some embodiments, the analogs include one, two, three, four, or five substitution, deletion or addition of amino acid residues as compared to the reference sequences. In some embodiments, the substitution is a conservative substitution.

As used herein the term "amino acid" refers to either natural and/or unnatural or synthetic amino acids, including glycine and both the D and L optical isomers, amino acid analogs and peptidomimetics. In some embodiments, non-natural amino acids are useful for tuning or engineering the helix or other secondary or tertiary structures of a peptide or protein for desired antimicrobial properties.

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table A.

TABLE A

| For Amino Acid | Replace With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S—Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S—Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Alternatively, non-limiting examples of conservative amino acid substitutions are provided in Table B below, where a similarity score of 0 or higher indicates conservative substitution between the two amino acids.

TABLE B

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

Alternatively, non-limiting examples of conservative amino acid substitutions include substitutions of a polar amino acid with a different polar amino acid, or substitutions of a hydrophobic amino acid with a different hydrophobic amino acid, as illustrated in Table C below. Each of the polar amino acids or hydrophobic amino acids, in some embodiments, can be substituted with Ala or Gly.

TABLE C

| Polar amino acids | K, R, H, E, D, N, Q, S, T (or substituted with A or G) |
|---|---|
| Hydrophobic amino acids | V, I, L, M, C, F, W, Y (or substituted with A or G) |

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

2. Antimicrobial Type II Bacteriocins

The present disclosure, in some embodiments, describes a computational approach for generating a systemic formula and related procedure to screen for new antimicrobial type-II bacteriocins. The identified protein and peptide families and their specific sequences are provided in Tables 2 and 3 and the appended Sequence Listing (SEQ ID NO:1-8, 9-327 and 328-1884). In some embodiments, provided is an isolated peptide comprising an amino acid sequence of Table 2 or 3 or the appended Sequence Listing (SEQ ID NO:1-1884) or an amino acid derived therefrom with one, two or three amino acid substitution. In some embodiments, the substitution is a conservative substitution. In some embodiments, the substitution is the replacement of a polar amino acid with a different polar amino acid, or the replacement of a hydrophobic amino acid with a different hydrophobic amino acid.

In some embodiments, provided is an isolated peptide comprising an amino acid sequence selected from the group consisting of EWGKQLGKWIGSKIK (SEQ ID NO: 1), KYVKNYLDFIKKAIDIFRPMPI (SEQ ID NO: 2), KWAKSAGKWIASKIK (SEQ ID NO: 3), KIGKTVG-TIVRKGFEIWSIFK (SEQ ID NO: 4), and an amino acid derived from SEQ ID NO: 1, 2, 3 or 4 with one, two or three amino acid substitution. In some embodiments, the peptide comprises an amino acid sequence selected from the group consisting of FKVIVTDAGHYPREWGKQLGKWIGSKIK (SEQ ID NO: 5), KRNYSIEKYVKNY1DFIKKAIDIFRPMPI (SEQ ID NO: 6), KTIATNATYYPNKWAKSAGKWIASKIK (SEQ ID NO: 7), QYDKTGYKIGKTVGTIVRKGFEIWSIFK (SEQ ID NO: 8), and an amino acid derived from SEQ ID NO: 5, 6, 7, or 8 with one amino acid substitution. In some embodiments, the substitution is a conservative substitution.

In some embodiments, the substitution is the replacement of a polar amino acid with a different polar amino acid, or the replacement of a hydrophobic amino acid with a different hydrophobic amino acid.

In some embodiments, the peptide is a fragment or fusion peptide described from natural proteins. In some embodiments, the peptide differs from natural proteins by at least an amino acid substation, addition or deletion.

In some embodiments, the peptide is not longer than 100 amino acid residues in length. In some embodiments, the peptide is not longer than 95, 90, 85, 80, 75, 70, 65, 60, 55, 50, 45, 40, 35, 30 or 25 amino acid resides in length. In some embodiments, the peptide has antimicrobial activity.

In some embodiments, the peptide has antimicrobial activity. In some embodiments, the peptides may be conjugated to therapeutic agents, prodrugs, peptides, proteins, enzymes, viruses, lipids, biological response modifiers, pharmaceutical agents, or PEG.

The peptides may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art. The peptides can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

3. Synthesis of Antimicrobial Peptides

The peptides described herein can be ordered from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification.

The peptides can be also prepared by using recombinant expression systems. Generally, this involves inserting the nucleic acid molecule into an expression system to which the molecule is heterologous (i.e., not normally present). One or more desired nucleic acid molecules encoding a peptide of the disclosure may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

4. Antimicrobial Compositions and Formulations

Compositions and formulations that include any one or more of the peptides as disclosed herein are also provided. In one embodiment, the composition includes any one or more of the peptides and a pharmaceutically acceptable carrier.

"Pharmaceutically acceptable carriers" refers to any diluents, excipients, or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in *Remington's Pharmaceutical Sciences*, Mack Publishing Company, a standard reference text in this field. They are preferably selected with respect to the intended form of administration, that is, oral tablets, capsules, elixirs, syrups and the like, and consistent with conventional pharmaceutical practices.

The pharmaceutical compositions of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this disclosure are formulated for pharmaceutical administration to a mammal, preferably a human being. Such pharmaceutical compositions of the disclosure may be administered in a variety of ways, preferably parenterally.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the disclosure. It should be understood that a specific dosage and treatment regimen for any particular patient will depend upon a variety of factors, including the activity of the specific peptide employed, the age, body weight, general health, sex and diet, renal and hepatic function of the patient, and the time of administration, rate of excretion, drug combination, judgment of the treating physician or veterinarian and severity of the particular disease being treated.

In some embodiments, the composition can further include a secondary antimicrobial agent. Non-limiting examples of such agents include imipenem, ceftazidime, colistin, chloroquine, artemisinin, vancomycin and daptomycin.

5. Therapeutic Methods

Methods of using the peptides, compositions and formulations of the present disclosure are also described. In one embodiment, the methods are for preventing or treating an infection of a microorganism. The microorganism can be a bacterium, such as a Gram-negative bacterium or a Gram-positive bacterium, a fungus, or a parasite.

The peptides, compositions and formulations are also useful for treating a disease or condition associated with an infection, such as wound abscess, catheter biofilm, pneumonia, and bacteremia.

In some embodiments, the treatment methods further include administration, concurrently or sequentially, of a second secondary antimicrobial agent. Non-limiting examples of such agents include imipenem, ceftazidime, colistin, chloroquine, artemisinin, vancomycin and daptomycin.

The peptides, compositions and formulations of the disclosure may be administered to the systemic circulation via parental administration. The term "parenteral" as used herein includes subcutaneous, intravenous, intramuscular, intra-articular, intra-synovial, intrasternal, intrathecal, intra-hepatic, intralesional and intracranial injection or infusion techniques. However, in cases where the infection is local (e.g., on the skin), the composition may be administered locally, such as topically.

6. Computational System and Methods

The present disclosure, in some embodiments, provides computer-implemented methods for identifying antimicrobial sequences and related systems and non-transitory computer-readable media. In one embodiment, a computer-implemented method of identifying a type-II bacteriocin is provided, as illustrated in FIG. 1 which is a process flow chart of a method 100. The various processing operations and/or data flows depicted in FIG. 1 (and in the other drawing figures) are described in greater detail herein. The described operations may be accomplished using some or all of the system components described in detail above and, in some implementations, various operations may be performed in different sequences and various operations may be omitted. Additional operations may be performed along with some or all of the operations shown in the depicted flow diagrams. One or more operations may be performed simultaneously. Accordingly, the operations as illustrated (and described in greater detail below) are exemplary by nature and, as such, should not be viewed as limiting.

In one embodiment, provided is a computer-implemented method of identifying a type-II bacteriocin. Optionally, at the first step, the method entails identifying a consensus formula from aligned type-II bacteriocin sequences (step 102). In a preferred embodiment, the consensus formula is not stringent so that more search results will be returned, which can be further filtered or screened. In some embodiment, the consensus formula comprises [LI]-[KREDNQSTYH]-X-[KREDNQSTYH]-X-[MLV]-X-X-[IVLT]-X-G-G, wherein X denotes any amino acid.

At step 104, the system or method searches in a protein database for proteins comprising a fragment matching the consensus formula for type-II bacteriocin (step 104). The protein database can be any database, data file, or data source that includes protein sequences. There are a number of publicly accessible protein databases available online. Matching a sequence to a formula can be done with methods known in the art.

At step 106, optionally, a hidden Markov model which can be developed based on known type-II bacteriocin sequences, can be used to search the database (step 106), in particular for unknown sequences. Methods of developing hidden Markov models and using them for sequence searches are known in the art. The search results from the hidden Markov model-based search can be pooled to the first search result.

It is the discovered herein that alpha-helical domain frequently co-exists with type-II bacteriocin domains in proteins. In some embodiments, accordingly, the search results are filtered to remove proteins that do not contain an alpha-helical domain (step 108). For instance, the alpha-helical domains can be identified with a consensus formula comprising X-[VILMCFWYAG]-[KRHEDNQSTAG]-[KRHEDNQSTAG]-[VILMCFWYAG]-[VILMCFWYAG]-[KRHEDNQSTAG]-[KRHEDNQSTAG]-[VILMCFWYAG]-X-[KRHEDNQSTAG]-[VILMCFWYAG], wherein X denotes any amino acid residue.

At step 110, optimally, a score can be calculated for the search results based on one or more parameters selected from hydrophobic moment, mean hydrophobicity, net charge, frequencies or ratio of K and R, or isoelectric point (step 110). In some embodiments, at least the hydrophobic moment is calculated. In some embodiments, at least the isoelectric point is calculated. In some embodiments, at least hydrophobic moment and isoelectric point are calculated, which can be optionally used for prioritizing, ranking, or selecting suitable type-II bacteriocins from the search results (step 112). Although not shown in FIG. 1, the selected type-II bacteriocins can be synthesized and tested in the lab.

Figure 6:
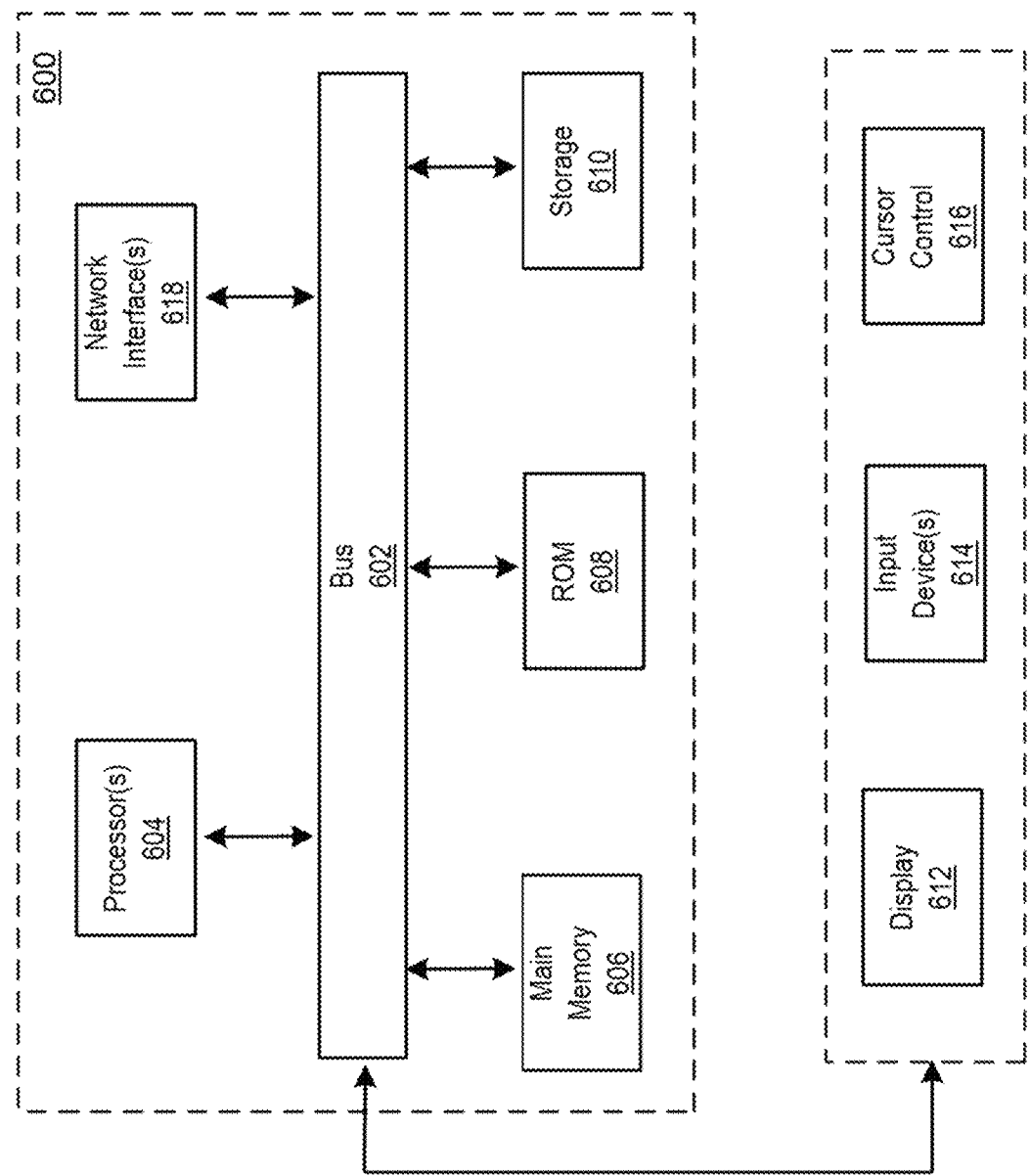
FIG. 6 illustrates a block diagram of an example computer system in which any of the implementations described herein may be implemented.

FIG. 6 depicts a block diagram of an example computer system 600 in which any of the embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 also includes a main memory 606, such as a random access memory (RAM), cache and/or other dynamic storage devices, coupled to bus 602 for storing information and instructions to be executed by processor 604. Main memory 606 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions.

The computer system 600 may be coupled via bus 602 to a display 612, such as a cathode ray tube (CRT) or LCD display (or touch screen), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 602. Transmission media can also take the form of acoustic or light waves, such as those generated during radio-wave and infra-red data communications.

Various forms of media may be involved in carrying one or more sequences of one or more instructions to processor 604 for execution. For example, the instructions may initially be carried on a magnetic disk or solid state drive of a remote computer. The remote computer can load the instructions into its dynamic memory and send the instructions over a telephone line using a modem. A modem local to computer system 600 can receive the data on the telephone line and use an infra-red transmitter to convert the data to an infra-red signal. An infra-red detector can receive the data carried in the infra-red signal and appropriate circuitry can place the data on bus 602. Bus 602 carries the data to main memory 606, from which processor 604 retrieves and executes the instructions. The instructions received by main memory 606 may retrieves and executes the instructions. The instructions received by main memory 606 may optionally be stored on storage device 610 either before or after execution by processor 604.

The computer system 600 also includes a communication interface 618 coupled to bus 602. Communication interface 618 provides a two-way data communication coupling to one or more network links that are connected to one or more local networks. For example, communication interface 618 may be an integrated services digital network (ISDN) card, cable modem, satellite modem, or a modem to provide a data communication connection to a corresponding type of telephone line. As another example, communication interface 618 may be a local area network (LAN) card to provide a data communication connection to a compatible LAN (or WAN component to communicated with a WAN). Wireless links may also be implemented. In any such implementation, communication interface 618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet". Local network and Internet both use electrical, electromagnetic or optical signals that carry digital data streams. The signals through the various networks and the signals on network link and through communication interface 618, which carry the digital data to and from computer system 600, are example forms of transmission media.

The computer system 600 can send messages and receive data, including program code, through the network(s), network link and communication interface 618. In the Internet example, a server might transmit a requested code for an application program through the Internet, the ISP, the local network and the communication interface 618.

The received code may be executed by processor 604 as it is received, and/or stored in storage device 610, or other non-volatile storage for later execution.

Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

Engines, Components, and Logic

Certain embodiments are described herein as including logic or a number of components, engines, or mechanisms. Engines may constitute either software engines (e.g., code embodied on a machine-readable medium) or hardware engines. A "hardware engine" is a tangible unit capable of performing certain operations and may be configured or arranged in a certain physical manner. In various example embodiments, one or more computer systems (e.g., a standalone computer system, a client computer system, or a server computer system) or one or more hardware engines of a computer system (e.g., a processor or a group of processors) may be configured by software (e.g., an application or application portion) as a hardware engine that operates to perform certain operations as described herein.

In some embodiments, a hardware engine may be implemented mechanically, electronically, or any suitable combination thereof. For example, a hardware engine may include dedicated circuitry or logic that is permanently configured to perform certain operations. For example, a hardware engine may be a special-purpose processor, such as a Field-Programmable Gate Array (FPGA) or an Application Specific Integrated Circuit (ASIC). A hardware engine may also include programmable logic or circuitry that is temporarily configured by software to perform certain operations. For example, a hardware engine may include software executed by a general-purpose processor or other programmable processor. Once configured by such software, hardware engines become specific machines (or specific components of a machine) uniquely tailored to perform the configured functions and are no longer general-purpose processors. It will be appreciated that the decision to implement a hardware engine mechanically, in dedicated and permanently configured circuitry, or in temporarily configured circuitry (e.g., configured by software) may be driven by cost and time considerations.

Accordingly, the phrase "hardware engine" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented engine" refers to a hardware engine. Considering embodiments in which hardware engines are temporarily configured (e.g., programmed), each of the hardware engines need not be configured or instantiated at any one instance in time. For example, where a hardware engine comprises a general-purpose processor configured by software to become a special-purpose processor, the general-purpose processor may be configured as respectively different special-purpose processors (e.g., comprising different hardware engines) at different times. Software accordingly configures a particular processor or processors, for example, to constitute a particular hardware engine at one instance of time and to constitute a different hardware engine at a different instance of time.

Hardware engines can provide information to, and receive information from, other hardware engines. Accordingly, the described hardware engines may be regarded as being communicatively coupled. Where multiple hardware engines exist contemporaneously, communications may be achieved through signal transmission (e.g., over appropriate circuits and buses) between or among two or more of the hardware engines. In embodiments in which multiple hardware engines are configured or instantiated at different times, communications between such hardware engines may be achieved, for example, through the storage and retrieval of information in memory structures to which the multiple hardware engines have access. For example, one hardware engine may perform an operation and store the output of that operation in a memory device to which it is communicatively coupled. A further hardware engine may then, at a later time, access the memory device to retrieve and process the stored output. Hardware engines may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented engines that operate to perform one or more operations or functions described herein. As used herein, "processor-implemented engine" refers to a hardware engine implemented using one or more processors.

Similarly, the methods described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Language

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

It will be appreciated that an "engine," "system," "data store," and/or "database" may comprise software, hardware, firmware, and/or circuitry. In one example, one or more software programs comprising instructions capable of being executable by a processor may perform one or more of the functions of the engines, data stores, databases, or systems described herein. In another example, circuitry may perform the same or similar functions. Alternative embodiments may comprise more, less, or functionally equivalent engines, systems, data stores, or databases, and still be within the scope of present embodiments. For example, the functionality of the various systems, engines, data stores, and/or databases may be combined or divided differently.

"Open source" software is defined herein to be source code that allows distribution as source code as well as compiled form, with a well-publicized and indexed means of obtaining the source, optionally with a license that allows modifications and derived works.

The data stores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

EXAMPLES

Example 1. Search and Testing of Type-II Bacteriocins

This example describes a method of searching for type-II bacteriocins and confirmation of the identified type-II bacteriocins having microbiocidal activities.

Among the earliest antimicrobial compounds first arose in prokaryotes themselves as means to defend against microbial competitors. Of these, well characterized members include class II bacteriocins, ribosomally-synthesized polypeptides produced primarily by Gram-positive bacteria. While a number of class II bacteriocins have been described, an expanding universe of bioinformatic datasets affords means by which to identify novel bacteriocin sequences from newly sequenced genomes. In the current investigation, a new search method was created to rapidly identify bacteriocin sequences with a high degree of fidelity. This multi-component method integrates the application of a relaxed bacteriocin signal peptide search term along with an amphipathic pattern search tool as a means to select for bacteriocin-like sequences. When applied, this method accurately identifies virtually all families of known class II bacteriocins. Moreover, the method retrieved a large number of sequences having structural features characteristic of ancient antimicrobial bacteriocins. Selected sequences identified by this search were synthesized and demonstrated to exert potent antimicrobial efficacy in vitro against a broad spectrum of human pathogens. These results represent discovery of new sequences and putative subclasses of type II bacteriocin may serve as physicochemical templates for innovative anti-infective therapeutic agents to meet the challenge of antibiotic resistance.

Methods and Materials

Identification of the Type IIa Bacteriocin Consensus Formula

To identify a consensus formula that was consistent with a majority of known class IIa bacteriocins, multiple sequence alignments with prototypic representatives of this family were carried out using CLUSTAL W, and further analyzed using MEGA 6. Sites of potential conservation were scored for specific residue or chemical identity to generate a 12 residue consensus formula. Several positions within the formula were degenerate depending on sequence or chemical (polar residues) conservation at individual sites.

Apply Method to Identify Putative Bacteriocins

Once this consensus formula was created, it was used with ScanProsite (**) to carry out a pattern search of the UniProtKB/Swiss-Prot and UniProtKB/TrEMBL databases. Search results were further limited as follows: 1) protein size (<80 residues); 2) bacterial organisms; and 3) localization of the pattern to the first 25 residues of the protein with a "<X(0,25)" logical operator.

Search for Amphipathic α-Helices Within Retrieved Dataset

Figure 3:
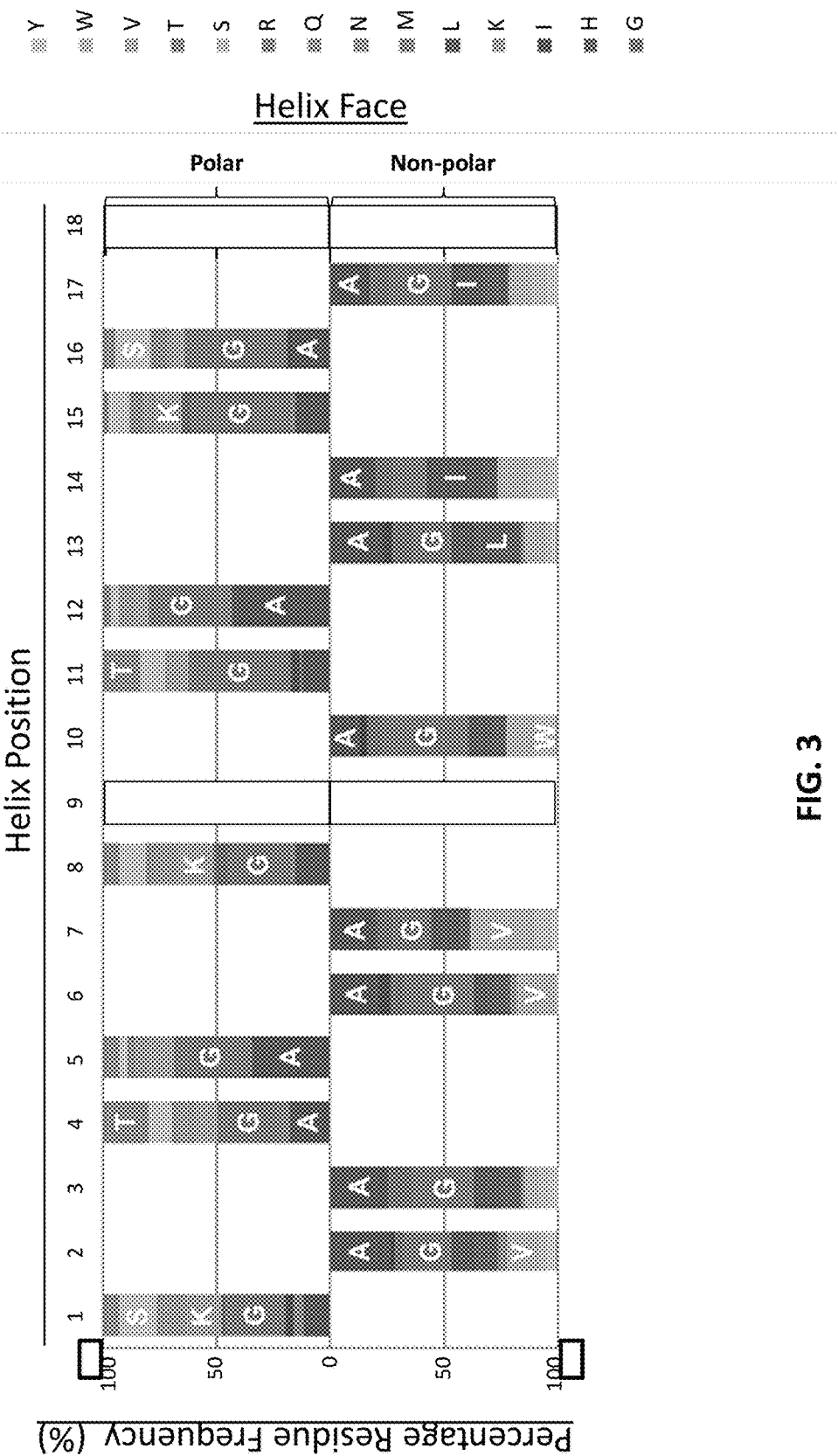
FIG. 3 shows positional and spatial amphipathic residue frequency. Percentages of individual residues on either the polar or non-polar peptide face of study peptides are represented as various color blocks. Residues above the x-axis are found on the polar face of retrieved peptides and residues below the axis are found on the non-polar face.

Results from the above database search were then formatted as per UniProtKB Swiss-Prot requirements and submitted as a sequence database against which additional pattern searches could be carried out. This database was then queried with a degenerate amphipathic sequence formula to scan for α-helical domains within retrieved protein dataset. The formula was advanced one position at a time through 18 iterations to represent an entire 18-residue helical wheel span (FIG. 3). Iteration 1 of this query sequence is listed below:

X-[VILMCFWYAG]-[KRHEDNQSTAG]-
[KRHEDNQSTAG]-[VILMCFWYAG]-
[VILMCFWYAG]-[KRHEDNQSTAG]-
[KRHEDNQSTAG]-[VILMCFWYAG]-X-
[KRHEDNQSTAG]-[VILMCFWYAG]

As the mature bacteriocin peptide is usually located near the C-terminus of the protein, search parameters included a "X(0,30)>" logical operator to restrict results to the final 30 residues of the protein.

Biophysical Parameter Determination

Retrieved datasets were subjected to batch analysis to compute the PI of individual sequences using ExPasy Compute PI/MW tool. Hydrophobic moment, mean hydrophobicity, net charge [K and R (+1), H (+0.5), D and E (−1)] and K and R residue frequency were determined using Python programs created for this purpose.

Operon Characterization

To probe for new, as yet unidentified, bacteriocins, the genomic regions surrounding uncharacterized hits were analyzed. A total of 20,000 base pairs (10,000 upstream and 10,000 downstream) from the identified sequence were scored for the presence of typical bacteriocin operon genes (ABC transporters, immunity proteins, pheromones) using the Ensembl Genomes REST API. Sequences that were found to be closely associated with bacteriocin-operon genes were prioritized for further study.

Peptide Synthesis

Select candidate microbicidal peptides were commercially synthesized by BioMatik at a level of >98% purity. Lyophilized peptides were reconstituted with ddIH20 and stored in aliquots at −20° C.

Assay for Antimicrobial Activity

Antimicrobial assays were performed using a well-established radial diffusion method modified to pH 5.5 or 7.5. A panel of microorganisms was tested: Gram-positive *Staphylococcus aureus* (ISP 479C, ISP 479R); Gram-negative *Salmonella typhimurium* (MS 5996s, MS 14028), *Pseudomonas aeruginosa* (PA01), *Acinetobacter baumanni* (17928) and the fungus *Candida albicans* (36082S, 36082R). Logarithmic phase organisms were inoculated ($10^6$ CFU/ml) into buffered agarose, and poured into plates. Peptides (10 μg) were introduced into wells in the seeded matrix, and incubated for 3 h at 37° C. Nutrient overlay medium was applied, and assays incubated at 37° C. or 30° C. for bacteria or fungi, respectively. After 24 h, zones of inhibition were measured. Independent experiments were repeated a minimum of two times.

Results

Identification of a Class II Bacteriocin Consensus Sequence Formula

To identify a signal peptide consensus formula that was consistent with a majority of known Class II (a-d) bacteriocins, multiple sequence alignments with prototypic representatives from these families were carried out. Initial alignments were generated using CLUSTAL W, followed by manual adjustment to align the double glycine motif using MEGA 6.

Analysis of these alignments revealed a number of conserved residues within the signal peptide domain that were used to generate a 12 residue consensus formula as follows:

```
 -12      -11     -10      -9      -8  -7  -6-5  -4   -3-2-1
[LI]-[KREDNQSTYH]-X-[KREDNQSTYH]-X-[MLV]-X-X-[IVLT]-X-G-G
```

As several positions within these alignments were conserved only at the physicochemical level (positions −9 and −11), they are represented by degenerate search terms reflecting the likelihood of a polar residue at these positions.

Primary Screen: Signal Peptide Method

The above formula was used as a ProSite query against the UniProtKB/Swiss-Prot and/TrEMBL databases and retrieved a total of 3050 sequences. Within this dataset the following classes of bacterial proteins were represented: 376 bacteriocins; 45 putative bacteriocins; 129 competence enhancing peptides; 7 pheromones; 12 autoinducing peptides; 170 putative bacteriocin related proteins; 182 other proteins; and 2129 uncharacterized sequences. All of the sequences are provided in the appended Sequence Listing, while a number of representative sequences are shown in Table 3 below.

In general, the majority of all sequences (bacteriocins and non-bacteriocins) retrieved with the signal peptide consensus were from Gram-positive Firmicutes (64%) and other Gram-positive organisms (Actinobacteria [2%], Deinococci [>1%]). Sequences were also retrieved from a number of Gram-negative organisms (Bacteroidetes [Chlorobi group, 13%], Chlamydia [>1%], Chloracidobacterium [>1%], Cyanobacteria [3%], Dehalococcoides [>1%], Fusobacteriales [>1%], Planctomycetia [>1%], Proteobacteria [17%]).

With respect to specificity, the formula retrieved a high percentage of the known Class II bacteriocin sequences. Notably, members from nearly all of the of Class IIa and IIb families were retrieved by the search. In particular, the formula identified representatives from approximately 90% of Class IIa families and 88% of Class IIb families. By comparison, many fewer of the cyclic, (13%) Class IIc, and other, (13%) Class IId, peptide groups were retrieved (Table 1). For many of the listed bacteriocins more than one representative of each family was retrieved. In some cases a large number of family members were retrieved such as for the class IIb Lactobin family where more than 90 members were identified.

TABLE 1

Bacteriocin Peptides Retrieved by Signal Consensus Formula Search

| Class | Peptide | | Organism |
|---|---|---|---|
| IIa | Acidocin | 8912, LF221B, M | Lactobacillus acidophilus |
| | Avicin | A | Enterococcus avium (Streptococcus avium) |
| | Carnobacteriocin | A, B2, BM1 | Carnobacterium maltaromaticum |
| | Curvacin | A | Lactobacillus curvatus |
| | Divergicin | 750 | Carnobacterium divergens (Lactobacillus divergens) |
| | Enterocin | B, 1071A/1B, CRL35, C2, NKR-5-3A/3Z, HF, Xbeta | Enterococcus faecium |
| | Leucocin | A, B, K, N, Q | Leuconostoc gelidum, Leconostoc carnosum, |
| | Mundticin | KS, L | Enterococcus pallens ATCC BAA-351 |
| | PapA | | Listeria aquatica FSL S10-1188 |
| | Piscicolin | 126 | Carnobacterium maltaromaticum |
| | Plantaricin | A, F, J, 1.25 beta, c81F | Lactobacillus plantarum |
| | Sakacin | A, D98c, P, X | Lactobacillus sakei |
| IIb | Amylovorin | L alpha, L beta | Lactobacillus amylovorus |
| | Bacteriocin | GatX, BacSJ2-8 | Streptococcus pneumoniae |
| | Brevicin | 925A | Lactobacillus brevis |
| | Gassericin | T | Lactobacillus gasseri |
| | Lactobin/Cerein | A/7B | Streptococcus australis ATCC 700641 |
| | Lactocin | 705 alpha, 705 beta | Lactobacillus curvatus |
| | Lactacin | F | Lactobacillus johnsonii |
| IId | Lactococcin | G | Clostridium perfringens (strain SM101/Type A) |
| | Mesentericin | B105, Y105 | Leuconostoc mesenteroides |
| | Weissellicin | L | Weissella hellenica |

Secondary Screen: Amphipathic Helix Method

As a refinement of this search, the retrieved sequences from the primary scan were formatted as a database, and a secondary screen with the amphipathic helix formula was carried out. In this case, the search was targeted to the final 30 residues of the peptide to probe for the presence of this motif within the mature portion of the peptide. When compared with the primary screen, this secondary screen provided information regarding the likelihood that retrieved peptides were α-helical in nature.

With this refinement, the total number of retrieved sequences was 1557 representing: 302 bacteriocins; 27 putative bacteriocins; 31 competence enhancing peptides; 1 pheromone; 11 autoinducing peptides; 78 putative bacteriocin related proteins; 65 other proteins; and 1042 uncharacterized sequences. Notably, while fewer sequences were retrieved with this secondary screen, the relative percentage of known bacteriocins within the characterized protein sub-dataset was increased from 41% to 53% of the returned sequences.

When the secondary alpha helical screen was applied to the dataset, nearly all of the Class IIa and IIb bacteriocin families were retrieved, suggesting that most of these peptides may be capable of adopting an α-helical conformation in membrane mimetic environments. One notable exception to this observation was for the pediocin sequences, which were not retrieved by the amphipathic sequence formula. However, this result may be expected, as many members of the pediocin-like bacteriocin group have been shown to form a hairpin-like structure at the C-terminus.

Residue Frequency within Bacteriocins

Given that the amphipathic sequence formula retrieves aligned datasets, peptides can be scored for the abundance of individual residues along an amphipathic helical span. When these alignments are carried out, the abundance of individual residues along both the predicted polar and non-polar faces of the retrieved helices can be calculated. In these studies, such alignments indicated that glycine was the most abundant residue at nearly all positions of these putative helical spans, whether present on the hydrophobic or hydrophilic face of the helix. In the few positions where glycine was not the most abundant residue, often the next most tiny and conformationally flexible residue, alanine, was present.

On the polar face of the peptide, after glycine and alanine the next most abundant residues were the cationic residue lysine and neutral hydrophilic residues threonine and serine. Notably, the cationic residue arginine was rarely found on the polar face of these bacteriocin amphipathic spans.

On the non-polar face the most abundant residues after glycine and alanine were valine, leucine and isoleucine. Tryptophan was also found with some abundance on this face at some positions, although tyrosine and phenylalanine were infrequently found in this analysis.

Analysis of Uncharacterized Sequences

Besides retrieving a significant number of known bacteriocin sequences, the amphipathic sequence method also identified a large number (~1042) of as yet uncharacterized sequences. If bacteriocins are represented to an equivalent degree between the characterized and uncharacterized datasets, it would be predicted that more than 550 of these unknown sequences may be novel bacteriocins (53% percent unknown=552).

As a means to characterize these unknown sequences, they were initially subjected to computational (Clustal W) and manual (MEGA 6) alignment (Supplemental Figure X). Unknown sequences were also scored for the following biophysical parameters: PI, net charge (Q), hydrophobic moment (μH), hydrophobicity (H) and arginine to lysine ratio ($N_R/N_K+N_R$).

Results from the above analyses were integrated, and four sequences (Table 2) from phylogenetically distinct organisms were chosen for further characterization (peptide name; SwissProt accession; species): peptide 1—A0RKV8 (*Bacillus thuringiensis*); peptide 2—D6E338 (*Eubacterium rectale*); peptide 3—B3ZXE9 (*Bacillus cereus*); peptide 4—R2S6C2 (*Enterococcus pallens*).

TABLE 2

Four identified peptide sequences, each along with a longer version, which was synthesized and tested

| No. | Name | Organism | Sequence | SEQ ID NO: |
|---|---|---|---|---|
| A0RKV8 (Peptide 1) | Uncharacterized protein | *Bacillus thuringiensis* (strain Al Hakam) | EWGKQLGKWI GSKIK | 1 |
| Peptide 1 - longer version | | | FKVIVTDAGH YPREWGKQLG KWIGSKIK | 5 |
| D6E338 (Peptide 2) | Uncharacterized protein | [*Eubacterium*] *rectale* DSM 17629 | KYVKNYLDFI KKAIDIFRPM PI | 2 |
| Peptide 2 - longer version | | | KRNYSIEKYV KNYlDFIKKA IDIFRPMPI | 6 |
| B3ZXE9 (Peptide 3) | Uncharacterized protein | *Bacillus cereus* 03BB108 | KWAKSAGKWI ASKIK | 3 |
| Peptide 3 - longer version | | | KTIATNATYY PNKWAKSAGK WIASKIK | 7 |

TABLE 2-continued

Four identified peptide sequences, each along with a longer version,
which was synthesized and tested

| R2S6C2 (Peptide 4) | Bacteriocin-type signal sequence | *Enterococcus pallens* ATCC BAA-351 | KIGKTVGTIV RKGFEIWSIF K | 4 |
|---|---|---|---|---|
| Peptide 4 - longer version | | | QYDKTGYKIG KTVGTIVRKG FEIWSIFK | 8 |

| No. | Count K | Count R | Q18 | Q Full | HM18 | HM18* Qfull | PI | HM*PI | H18 | Charge | µH |
|---|---|---|---|---|---|---|---|---|---|---|---|
| A0RKV8 | 4 | 0 | 3 | 3 | 0.58 | 1.7 | 10 | 5.81 | 0.33 | +3.5 | 0.48 |
| D6E338 | 4 | 1 | 3 | 3 | 0.67 | 2.03 | 5.18 | 3.52 | 0.39 | +4 | 0.41 |
| B3ZXE9 | 5 | 0 | 5 | 5 | 0.50 | 2.51 | 9.94 | 5.00 | 0.26 | +6 | 0.35 |
| R2S6C2 | 3 | 1 | 3 | 4 | 0.58 | 2.34 | 9.46 | 5.54 | 0.43 | +4 | 0.44 |

Figure 2:
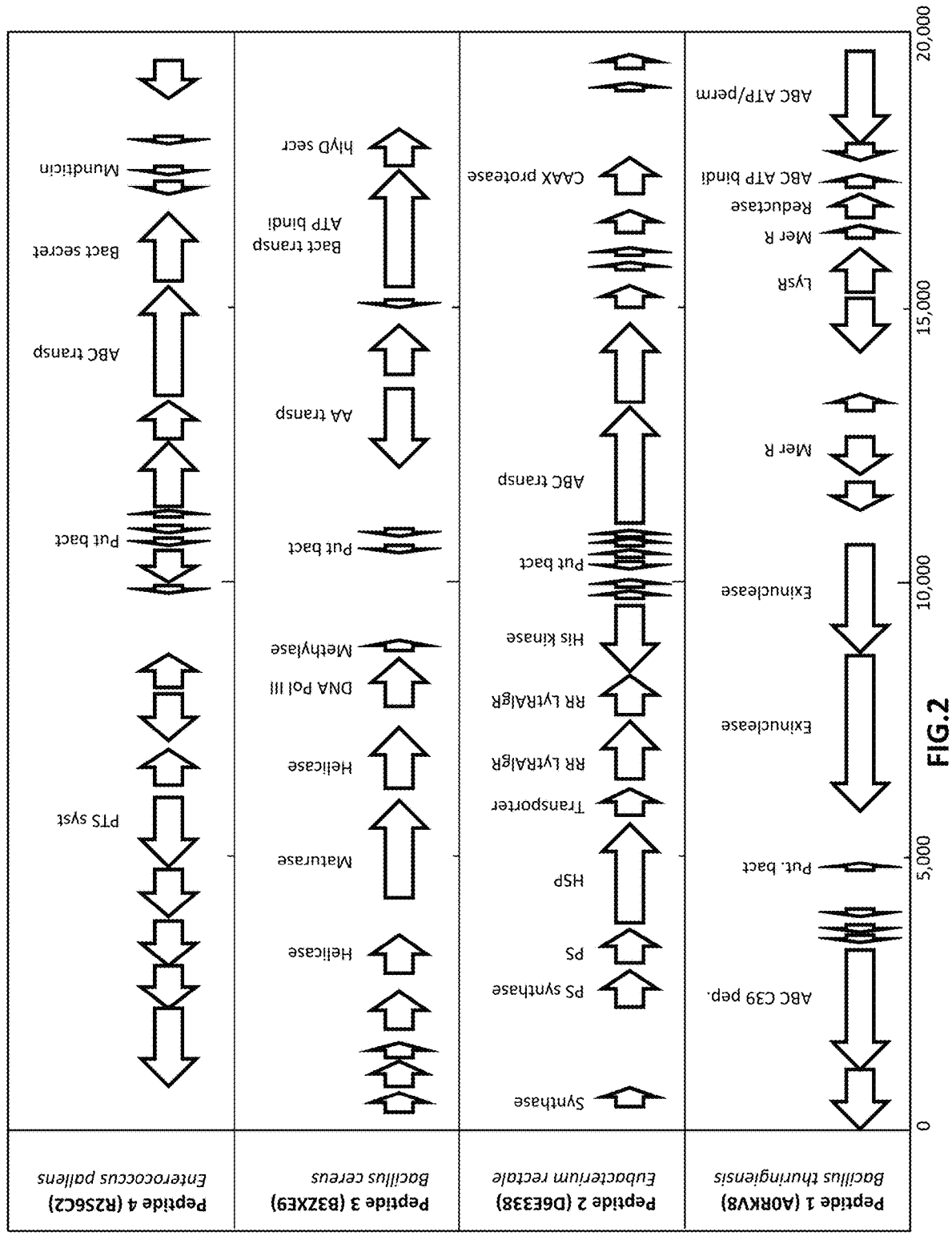
FIG. 2 shows the genomic environment surrounding putative bacteriocins. Analysis of 20 kb region surrounding putative bacteriocin genes. Red—putative bacteriocin; gray—hypothetical proteins; dark blue—C39 bacteriocin processing peptidase; medium blue—exinuclease ABC subunit; light blue—ABC transporter, ATP binding protein; green other enzyme; purple—polymerase related protein.

At the genetic level, peptides 1-4 were localized to bacteriocin-like operon regions containing ABC transporters and other bacteriocin-associated genes (FIG. 2). In particular, all were localized within 20 kb of an ABC transporter protein, as well as ABC transporter accessory genes such as C39 peptidases and ATP binding proteins. Many of the putative bacteriocins were also localized within clusters of small genes that resembled other bacteriocin sequences and/or pheromones. In some cases, prototypic bacteriocin immunity peptides were also localized within the putative bacteriocin operons.

Figure 4:
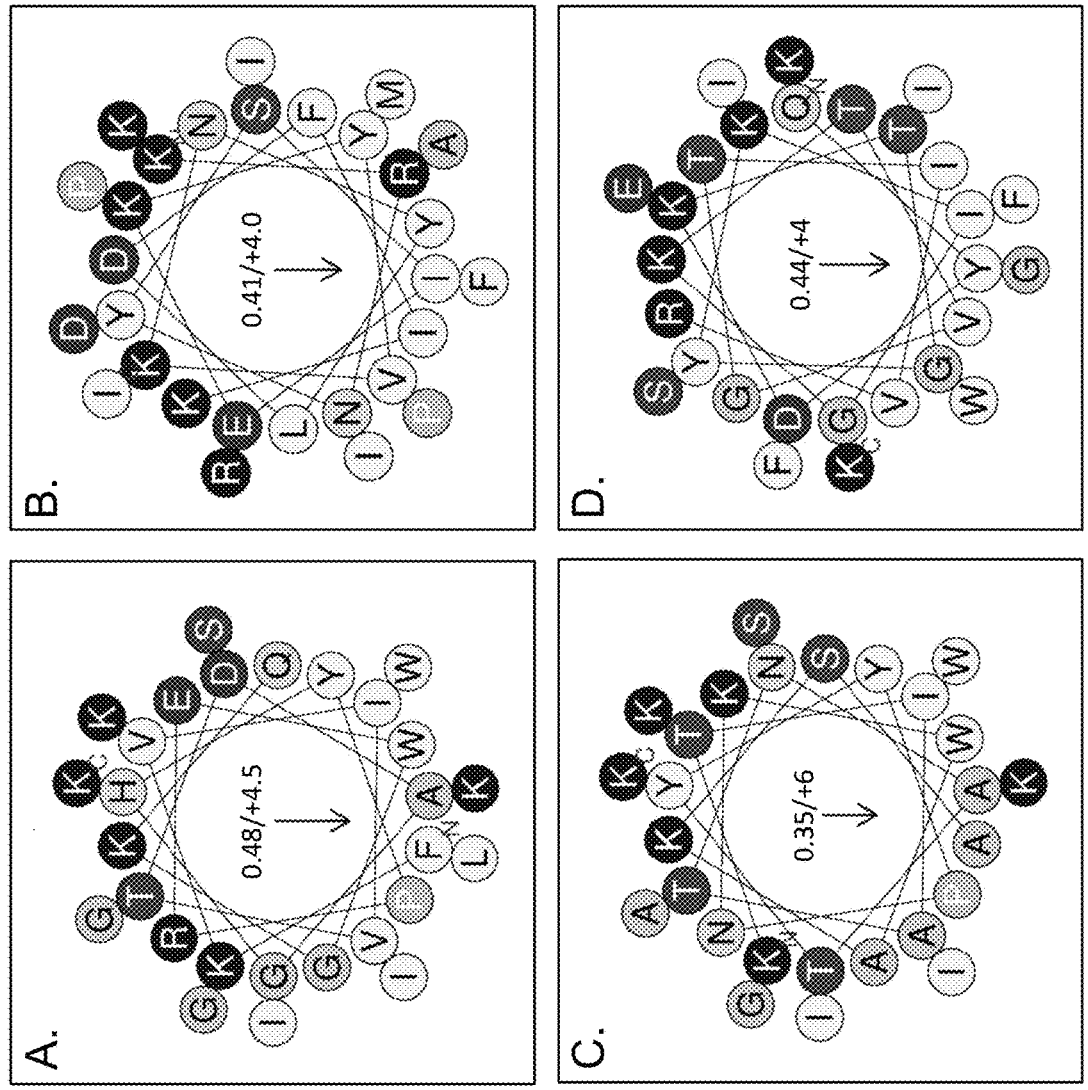
FIG. 4, with panels A-D, shows helical wheel analysis and biophysical properties of putative bacteriocins. Putative bacteriocins synthesized for assessment of antimicrobial activity. Arrows hydrophobic moment and direction. A. Peptide 1: A0RKV8 (+4.5), PI—10.7; *Bacillus thuringiensis* (G+); FKVIVTDAGHYPREWGKQLGKWIGSKIK, SEQ ID NO: 5 (28). B. Peptide 2: D6E338 (+4), PI 10.3; *Eubacterium rectale*; KRNYSIEKYVKNY1DFIKKAIDIFRPMPI, SEQ ID NO: 6 (29). C. Peptide 3: B3ZXE9 (+6), PI—10.9; *Bacillus cereus*; KTIATNATYYPNKWAKSAGKWIASKIK, SEQ ID NO: 7 (27). D. Peptide 4: R2S6C2 (+4), PI—10.5; *Enterococcus pallens*, QYDKTGYKIGKTVGTIVRKG-FEIWSIFK, SEQ ID NO: 8 (28).

As a further means of characterization, peptides 1-4 were synthesized so that their microbicidal properties could be determined. This assessment revealed that all four putative bacteriocins possessed microbicidal activity against Gram positive (*S. aureus*), Gram negative (*S. typhimurium, P. aeruginosa, A. baumanni*) and fungal (*C. albicans*) organisms (FIG. 4). While active against all classes of microbes, peptides 1-4 were generally more potent towards Gram negative microorganisms than the other organisms in this study (FIG. 4).

As a test of the relative activity of these putative bacteriocins in blood versus phagolysosomal/wound septic environments, microbicidal assays were carried out in representative physiologic buffers at pH 7.5 and 5.5 respectively. In general, peptides 1-4 were typically more active at pH 7.5 than at pH 5.5, and notably peptide 3 lost nearly all of its activity against Gram positive *S. aureus* at pH 5.5.

Taken together, given their localization to bacteriocin-like operons and potent microbicidal spectrum, it seems likely that peptides 1-4 represent novel bacteriocin sequences. However, studies to isolate these putative sequences will be necessary to confirm this observation.

TABLE 3

Representative peptides identifies from the primary screen

| Accession # | Name | Comp Form Match | HM | Q | HMQ | PI | SEQ ID NO: |
|---|---|---|---|---|---|---|---|
| A1ZN33 | Uncharacterized protein | RQMVRHLRRFMRRYGRC | 0.70 | 7.5 | 5.27 | 7.93 | 9 |
| A0A0A1GSN1 | Uncharacterized protein | KNGLKKFFKWVRKL | 0.75 | 6 | 4.49 | 10.59 | 10 |
| D9SR34 | Uncharacterized protein | SLKKALKKAVSGLGKIIK | 0.66 | 6 | 3.99 | 9.6 | 11 |
| L7ZAD1 | Putative peptide pheromone/induction peptide | KTLTKFFKSLIKR | 0.72 | 5 | 3.58 | 10.36 | 12 |
| K9E5B5 | Uncharacterized protein | RCRKVYHRLWGK | 0.61 | 5.5 | 3.33 | 9.3 | 13 |
| D9SV22 | Uncharacterized protein | SLRKALKKIIDAIVK | 0.72 | 4 | 2.88 | 9.82 | 14 |
| K0NDW4 | Uncharacterized protein | SQLYKNLFKVFRK | 0.69 | 4 | 2.75 | 10.41 | 15 |
| I6WB56 | Putative plantaricin A peptide | LQMGATAIKQVKKLFKKWG | 0.55 | 5 | 2.74 | 10.48 | 16 |
| D1P3A0 | Uncharacterized protein | YKNVKAFIEKCRKVY | 0.64 | 4 | 2.54 | 9.24 | 17 |
| Q38Y68 | Putative bacteriocin inducing peptide | REYLNKITKWIKH | 0.71 | 3.5 | 2.48 | 9.92 | 18 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| C2SB64 | Uncharacterized protein | WIGKVGKQYKKAT | 0.59 | 4 | 2.34 | 9.33 | 19 |
| R5IRG3 | Uncharacterized protein | GSIISSIVRGGILILELGRSFGSALRRLLKK | 0.45 | 5 | 2.24 | 10.01 | 20 |
| B1SE87 | Bacteriocin-type signal sequence | RQAAKAIGKAVGKLF | 0.55 | 4 | 2.22 | 9.78 | 21 |
| U2JCR9 | Bacteriocin-type signal sequence | MRNGFEIFKKIAKSIIDAFRHA | 0.62 | 3.5 | 2.16 | 8.09 | 22 |
| R2SSG8 | Bacteriocin-type signal sequence | AVGKNVWEFGKGFVKGWNKAK | 0.51 | 4 | 2.02 | 10.09 | 23 |
| R2S6C2 | Bacteriocin-type signal sequence | KTGYKIGKTVGTIVRKGFEIWS | 0.50 | 4 | 2.01 | 9.46 | 24 |
| E3R2A6 | Uncharacterized protein | GGSKGWNKFWKS | 0.64 | 3 | 1.93 | 9.52 | 25 |
| K1N8K9 | Uncharacterized protein | GGSKGWNKFWKS | 0.64 | 3 | 1.93 | 9.52 | 26 |
| D7V8H5 | Uncharacterized protein | GGGAWKNFWSSLRKGF | 0.62 | 3 | 1.86 | 9.99 | 27 |
| R9X316 | Uncharacterized protein | KQWYRLGERVGRVA | 0.62 | 3 | 1.85 | 9.69 | 28 |
| E7S5Z7 | Uncharacterized protein | GSACAYMRRVCKK | 0.46 | 4 | 1.84 | 9.1 | 29 |
| E8KCS4 | Bacteriocin-type signal sequence | RRITSFFANLFQK | 0.61 | 3 | 1.84 | 9.99 | 30 |
| A4BNK7 | Uncharacterized protein | QKAMKNIRGGARG | 0.44 | 4 | 1.77 | 11.91 | 31 |
| D3H665 | Excreted peptide | VKWCNKLFGTGRHVA | 0.50 | 3.5 | 1.74 | 4.43 | 32 |
| C2CZ62 | Bacteriocin-type signal sequence | LSHISGGVTRYRHHEKKSWIDDFMKGFKK | 0.31 | 5.5 | 1.73 | 6.82 | 33 |
| I0SA65 | Uncharacterized protein | SITNFWKKYFNH | 0.69 | 2.5 | 1.72 | 5.45 | 34 |
| I0T6B7 | Uncharacterized protein | SITNFWKKYFNH | 0.69 | 2.5 | 1.72 | 5.45 | 35 |
| R6SQB3 | Uncharacterized protein | YNPFKNIFHRFSNGH | 0.57 | 3 | 1.71 | 10.82 | 36 |
| K8WE53 | Uncharacterized protein | YKNVKAFIEKCRS | 0.56 | 3 | 1.69 | 9.17 | 37 |
| G0IAI7 | Uncharacterized protein | GRFFGGIYNAGRSFGRNV | 0.56 | 3 | 1.68 | 9.22 | 38 |
| A0A0E2PPW4 | Bacteriocin-type signal sequence | GRFFGGIYNAGRSFGRNV | 0.56 | 3 | 1.68 | 9.22 | 39 |
| G6A7G8 | Uncharacterized protein | RGIIGIGKKLFG | 0.55 | 3 | 1.66 | 9.7 | 40 |
| R7KCN7 | Uncharacterized protein | GTILNQLNKLISILVDSGKSLGSSIRRIS | 0.55 | 3 | 1.65 | 8.98 | 41 |
| A0A0B5ZQ16 | Uncharacterized protein | INGGKTIATNATYYPNKWAKSVGKWIAS | 0.41 | 4 | 1.63 | 9.94 | 42 |
| G6CHH9 | Bacteriocin-type signal sequence domain protein | SNFIHKIKQIFTH | 0.54 | 3 | 1.62 | 9.82 | 43 |
| Q5FI67 | Uncharacterized protein | IGGSAKSYIRRLG | 0.54 | 3 | 1.61 | 9.69 | 44 |
| R6Y309 | Uncharacterized protein | GSLFSALAKGFNVFVDMGRALGSSIRRLVNN | 0.53 | 3 | 1.58 | 9.18 | 45 |
| C0WN46 | Bacteriocin-type signal sequence | LSHISGGVTRYRYHEKKSWIDDFMKGFKK | 0.32 | 5 | 1.58 | 6.82 | 46 |
| C0XJC5 | Bacteriocin-type signal sequence | LSHISGGVTRYRYHEKKSWIDDFMKGFKK | 0.32 | 5 | 1.58 | 6.82 | 47 |
| R5Y709 | Uncharacterized protein | AAFINGVKGIFSIFFDFGNSLGSSIRRIK | 0.52 | 3 | 1.57 | 9.9 | 48 |
| U2YG00 | Uncharacterized protein | RGMIGIGKKLFG | 0.51 | 3 | 1.52 | 9.63 | 49 |
| R5IWG8 | Uncharacterized protein | ATFINAIVKGLSLIIELGKSLGSSFRRIT | 0.50 | 3 | 1.51 | 9.51 | 50 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| B3ZXE9 | Uncharacterized protein | INGGKTIATNATYYPNKWAKSAGKWIAS | 0.38 | 4 | 1.51 | 9.94 | 51 |
| B6W9P3 | Bacteriocin-type signal sequence | QIYKEAKDFVNNRAGNLIRGFKDVWKN | 0.49 | 3 | 1.48 | 9.1 | 52 |
| A0A075JT42 | Uncharacterized protein | LSRVKGGMSRIAG | 0.49 | 3 | 1.46 | 9.3 | 53 |
| C2MRT0 | Uncharacterized protein | KWGKELGRWIGS | 0.73 | 2 | 1.46 | 10.09 | 54 |
| A0RKV8 | Uncharacterized protein | REWGKQLGKWIGS | 0.71 | 2 | 1.41 | 10 | 55 |
| G2G092 | Bacteriocin-type signal sequence domain protein | SGGGKFIGNLIKLARP | 0.44 | 3 | 1.33 | 10.49 | 56 |
| F9D2A0 | Uncharacterized protein | LRFLDRIMGGFRQ | 0.66 | 2 | 1.32 | 11.55 | 57 |
| A0A059KSD2 | Uncharacterized protein | FGGLLRHLFGFK | 0.52 | 2.5 | 1.31 | 9.9 | 58 |
| S3ZDV9 | Uncharacterized protein | LPNLGRRMVGAW | 0.65 | 2 | 1.31 | 10.55 | 59 |
| F7QWM3 | Uncharacterized protein | LSHVNGGYNRLAGRIGHYT | 0.44 | 3 | 1.31 | 9.52 | 60 |
| W9BZA4 | Uncharacterized protein | IGGLLGGIFGLLRK | 0.65 | 2 | 1.30 | 9.13 | 61 |
| A0A0E4FN40 | Uncharacterized protein | RNGARIAGRLVGIA | 0.43 | 3 | 1.29 | 5.11 | 62 |
| G8UJS1 | Uncharacterized protein | RNGARIAGRLVGIA | 0.43 | 3 | 1.29 | 5.11 | 63 |
| R4LKG1 | Uncharacterized protein | ANHANGLFRRVL | 0.51 | 2.5 | 1.27 | 5.56 | 64 |
| A9EDI1 | Uncharacterized protein | FSKLQKLIGGVEK | 0.63 | 2 | 1.25 | 9.73 | 65 |
| D5BXP3 | Uncharacterized protein | AARRAFASGRKA | 0.31 | 4 | 1.25 | 10.83 | 66 |
| A0A081QIR4 | Uncharacterized protein | GIAGVLNAAVQIFNAGYKFGSDFARRGR | 0.41 | 3 | 1.24 | 4.99 | 67 |
| A0A0F3HMJ4 | Uncharacterized protein | GIAGVLNAAVQIFNAGYKFGSDFARRGR | 0.41 | 3 | 1.24 | 4.99 | 68 |
| G0IAJ8 | Uncharacterized protein | GIAGVLNAAVQIFNAGYKFGSDFARRGR | 0.41 | 3 | 1.24 | 4.99 | 69 |
| A0A086B184 | Uncharacterized protein | GKSCWKILKDLIGL | 0.62 | 2 | 1.24 | 9.6 | 70 |
| A0A0F2CT49 | Uncharacterized protein | GIAGVLNAAVQIFNAGYKFGSDLARRGR | 0.41 | 3 | 1.24 | 4.99 | 71 |
| A8SCT0 | Uncharacterized protein | IGKVFNYIARIFSGASSIIN | 0.62 | 2 | 1.23 | 4.94 | 72 |
| D4K7U6 | Uncharacterized protein | IGKVFNYIARIFSGASSIIN | 0.62 | 2 | 1.23 | 4.94 | 73 |
| Q040A1 | Uncharacterized protein | VAKDAWNHLDQIRSGWRKAGNS | 0.48 | 2.5 | 1.20 | 9.3 | 74 |
| A0A0A2CDF7 | Uncharacterized protein | KTYKKVAKKIEDYVDNGP | 0.58 | 2 | 1.16 | 4.81 | 75 |
| F8HC99 | Uncharacterized protein | FSSGYKFGTDLARRGR | 0.38 | 3 | 1.15 | 9.6 | 76 |
| F8LGE1 | Uncharacterized protein | FSSGYKFGTDLARRGR | 0.38 | 3 | 1.15 | 9.87 | 77 |
| T0TBH8 | Uncharacterized protein | TTLLTGVFGWLKKF | 0.57 | 2 | 1.13 | 6.54 | 78 |
| C7H4R6 | Uncharacterized protein | VGKLFNYIARVFSAGSSIVN | 0.54 | 2 | 1.09 | 4.66 | 79 |
| F8N9W8 | Uncharacterized protein | IDSFKKGADKANR | 0.54 | 2 | 1.09 | 4.83 | 80 |
| A0A077E9X6 | Uncharacterized protein | KKGLRQITGGME | 0.54 | 2 | 1.09 | 8.84 | 81 |
| E2ZM85 | Uncharacterized protein | NVGKVFNAIARIFSGASS | 0.54 | 2 | 1.07 | 4.99 | 82 |
| R4KBP7 | Uncharacterized protein | VKNLFNQISQVQQKTAQEFQQMMNKFPQ | 0.53 | 2 | 1.06 | 6.12 | 83 |
| U2J1M1 | Uncharacterized protein | GGNWINVFKSVVDIARRG | 0.52 | 2 | 1.05 | 9.4 | 84 |
| A0A0G0A6F6 | Uncharacterized protein | TSLESLGSRARRVLKEIS | 0.52 | 2 | 1.05 | 9.81 | 85 |
| R7F343 | Uncharacterized protein | GSLLNAFVDILKVLLDAGRSVGSGIRRAT | 0.52 | 2 | 1.04 | 9.1 | 86 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| Q8RTK6 | Uncharacterized protein | KTLATVIGGGKGGGILSWFIGESSDIWKGFKKGMNHYNK | 0.23 | 4.5 | 1.03 | 9.7 | 87 |
| U2XMS3 | Uncharacterized protein | KTLATVIGGGKGGGILSWFIGESSDIWKGFKKGMNHYNK | 0.23 | 4.5 | 1.03 | 9.7 | 88 |
| R5MS15 | Uncharacterized protein | GSILNSFIRYVNVFFEIGQAFGSAIRR | 0.51 | 2 | 1.02 | 9.92 | 89 |
| D2JC35 | Uncharacterized protein | GEKIGKLLREVREAK | 0.51 | 2 | 1.02 | 9.22 | 90 |
| F7QWF6 | Uncharacterized protein | IVQGAVAVFKSGYRH | 0.41 | 2.5 | 1.01 | 9.9 | 91 |
| H3NCZ5 | Uncharacterized protein | TVGGSYSSACKRVWNAK | 0.34 | 3 | 1.01 | 10.12 | 92 |
| R5MUU1 | Uncharacterized protein | ATFFNALARSLSTISDIGRSLGTAIR | 0.50 | 2 | 1.01 | 10.44 | 93 |
| R6GW12 | Uncharacterized protein | TQMINSFVKLVSTLLDLGRTMGSALR | 0.50 | 2 | 0.99 | 10.01 | 94 |
| R6C487 | Uncharacterized protein | SVGTIINAVVKAISLLNELGQQLGSAIRR | 0.48 | 2 | 0.95 | 9.74 | 95 |
| A0A0F4NQ60 | Uncharacterized protein | SGPAWLSRYLHK | 0.38 | 2.5 | 0.95 | 5.28 | 96 |
| Q5FI70 | Uncharacterized protein | VGRGLWENLSNIFKH | 0.62 | 1.5 | 0.93 | 10.35 | 97 |
| X5CZ49 | Putative inducing factor protein | THLLAGLWDWFKR | 0.60 | 1.5 | 0.91 | 5.38 | 98 |
| R9JDF1 | Uncharacterized protein | SSVKQFFEKGARSA | 0.45 | 2 | 0.89 | 6.7 | 99 |
| E1TJ04 | Uncharacterized protein | AAHRAIAKVAAT | 0.36 | 2.5 | 0.89 | 10.89 | 100 |
| A7GJQ0 | Uncharacterized protein | TGFYNGYRNAGR | 0.44 | 2 | 0.88 | 5.5 | 101 |
| A0A0A5I2E5 | Uncharacterized protein | SGPAWLNRYLNK | 0.44 | 2 | 0.88 | 4.73 | 102 |
| A0A0H2MUQ5 | Uncharacterized protein | SGPAWLNRYLNK | 0.44 | 2 | 0.88 | 4.71 | 103 |
| F9T9J1 | Uncharacterized protein | SGPAWLNRYLNK | 0.44 | 2 | 0.88 | 4.71 | 104 |
| R6FA54 | Uncharacterized protein | KVKQFFEKGARSAME | 0.44 | 2 | 0.88 | 6.55 | 105 |
| R6W634 | Uncharacterized protein | KVKQFFEKGARSAME | 0.44 | 2 | 0.88 | 6.05 | 106 |
| R2P4R2 | Bacteriocin-type signal sequence | NNLSKGGAKCGAAIAGGL | 0.44 | 2 | 0.87 | 9.39 | 107 |
| A0A086B186 | Uncharacterized protein | KEILTHVKGGAAGSGYINTVSGECNSSGRSCWKALKDLLG | 0.34 | 2.5 | 0.86 | 9.7 | 108 |
| U2I0Q7 | Uncharacterized protein | QGGGVIGRLIKAAANA | 0.43 | 2 | 0.86 | 5.1 | 109 |
| A0A0D6XRS2 | Uncharacterized protein | GWAGRIAGKVAGGVRSLADG | 0.43 | 2 | 0.86 | 5.13 | 110 |
| R9N5C7 | Uncharacterized protein | TQVKQFFEKGAKSA | 0.43 | 2 | 0.85 | 7.89 | 111 |
| U2QX19 | Uncharacterized protein | QQLVTLIRGGCAKIIA | 0.42 | 2 | 0.85 | 10.56 | 112 |
| G6F0H8 | Uncharacterized protein | ANIIRTGLKNGDNWATIGKNIG | 0.42 | 2 | 0.85 | 10.29 | 113 |
| R7IG68 | Uncharacterized protein | LDSINGGGKKLWYLLGAGLSFFLGLFSGLVNPVKC | 0.42 | 2 | 0.84 | 7.9 | 114 |
| R6SN80 | Uncharacterized protein | MKTCKGCGASILST | 0.42 | 2 | 0.84 | 8.75 | 115 |
| C9QIT0 | Uncharacterized protein | NGPAWLNRYLTK | 0.41 | 2 | 0.83 | 4.9 | 116 |
| A3HWV0 | Putative bacteriocin-type signal sequence | VSTARKLGRDFGDFLAYCAVVSIFIADAAKDAIKTFTKL | 0.41 | 2 | 0.83 | 7.87 | 117 |
| A0A0J1CUK6 | Uncharacterized protein | QALRSYAKPAGS | 0.41 | 2 | 0.81 | 10.67 | 118 |
| E7S5Z5 | Uncharacterized protein | LKSIKGGGDTVFDKVNHFF | 0.53 | 1.5 | 0.80 | 9.14 | 119 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| A0A075SGV6 | Bacteriocin-type signal sequence | LKSIKGGGDTVFDKVNHFF | 0.53 | 1.5 | 0.80 | 9.44 | 120 |
| A0A0A2YHL6 | Uncharacterized protein | SISSGLTAGYSLVRR | 0.38 | 2 | 0.77 | 4.6 | 121 |
| U1I9V8 | Uncharacterized protein | SISSGLTAGYSLVRR | 0.38 | 2 | 0.77 | 4.6 | 122 |
| X8JLI8 | Bacteriocin-type signal sequence | VINEFVKGFRQAW | 0.75 | 1 | 0.75 | 5.05 | 123 |
| A0A074JK52 | Signal peptide protein | VINEFVKGFRQAW | 0.75 | 1 | 0.75 | 5.05 | 124 |
| E4S7K8 | Uncharacterized protein | LGKLYKWITNVIDNIF | 0.74 | 1 | 0.74 | 7.79 | 125 |
| G2SRZ9 | Putative bacteriocin | SVNRWGAAVGTGGKA | 0.37 | 2 | 0.74 | 9.59 | 126 |
| A0A077KSQ4 | Uncharacterized protein | KGGNKAITPVREG | 0.37 | 2 | 0.74 | 9.78 | 127 |
| A0A0C1TV13 | Uncharacterized protein | IYDGVKAAVNKLAHT | 0.49 | 1.5 | 0.74 | 6.03 | 128 |
| A0A073BCT9 | Uncharacterized protein | QRVHAACNELLRGQ | 0.48 | 1.5 | 0.72 | 7.73 | 129 |
| U2PR16 | Uncharacterized protein | GDSYLQKLTGIRRHRLRALFGGGEE | 0.29 | 2.5 | 0.72 | 6.53 | 130 |
| E3CPS1 | Bacteriocin-type signal sequence | VINEFVKGFHHAW | 0.70 | 1 | 0.70 | 5.43 | 131 |
| E8KT23 | Bacteriocin-type signal sequence | VINEFVKGFHHAW | 0.70 | 1 | 0.70 | 5.43 | 132 |
| I7KH06 | Uncharacterized protein | AGYTIGKDIAKR | 0.35 | 2 | 0.69 | 4.51 | 133 |
| A0A015XA39 | Uncharacterized protein | YNKMEKILEKLS | 0.69 | 1 | 0.69 | 4.77 | 134 |
| A0A015YJT2 | Uncharacterized protein | YNKMEKILEKLS | 0.69 | 1 | 0.69 | 4.77 | 135 |
| A0A015Z6Y8 | Uncharacterized protein | YNKMEKILEKLS | 0.69 | 1 | 0.69 | 4.77 | 136 |
| A0A016GFI9 | Uncharacterized protein | YNKMEKILEKLS | 0.69 | 1 | 0.69 | 4.77 | 137 |
| A0A017PDT5 | Uncharacterized protein | YNKMEKILEKLS | 0.69 | 1 | 0.69 | 4.77 | 138 |
| A0A0E2B796 | Uncharacterized protein | YNKMEKILEKLS | 0.69 | 1 | 0.69 | 4.77 | 139 |
| K1G3D7 | Uncharacterized protein | YNKMEKILEKLS | 0.69 | 1 | 0.69 | 4.49 | 140 |
| K1G6C4 | Uncharacterized protein | YNKMEKILEKLS | 0.69 | 1 | 0.69 | 4.49 | 141 |
| D6E338 | Uncharacterized protein | SIEKYVKNYLDFIKKAID | 0.69 | 1 | 0.69 | 5.18 | 142 |
| F4KYL7 | Uncharacterized protein | HKVADTYNAIAKT | 0.46 | 1.5 | 0.69 | 4.78 | 143 |
| U2DX84 | Bacteriocin-type signal sequence | GGNIFKSIWNWIKE | 0.67 | 1 | 0.67 | 8.23 | 144 |
| A0RKV6 | Uncharacterized protein | VIGIIAGGAAIIDYGNDFVKGAKKGAK | 0.34 | 2 | 0.67 | 9.4 | 145 |
| K9EK75 | Uncharacterized protein | ARGAKEAVDRIRI | 0.34 | 2 | 0.67 | 7.63 | 146 |
| A0A0D5BK00 | Uncharacterized protein | APGGCRSIAGAGPK | 0.33 | 2 | 0.67 | 8.83 | 147 |
| T0Q2K8 | Uncharacterized protein | APGGCRSIAGAGPK | 0.33 | 2 | 0.67 | 8.59 | 148 |
| T0V1T0 | Uncharacterized protein | SWANYLSRYLKE | 0.67 | 1 | 0.67 | 7.98 | 149 |
| G2JCE9 | Bacteriocin-type signal sequence | LGKAYKWIANLIESIF | 0.67 | 1 | 0.67 | 7.95 | 150 |
| A0A077EH26 | Uncharacterized protein | APGGCRSLAGAGPK | 0.33 | 2 | 0.66 | 8.59 | 151 |
| A0A098G366 | Uncharacterized protein | SGGNRVHEGFDRMR | 0.44 | 1.5 | 0.66 | 11.57 | 152 |
| S9P0Z7 | Uncharacterized protein | GGGRGGRDGRGGRGGRGGRGGRGGY | 0.09 | 7 | 0.66 | 6.18 | 153 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| D4BZB4 | Uncharacterized protein | NRLVQVVGGWLHSFAL | 0.43 | 1.5 | 0.65 | 9.3 | 154 |
| D4BZB5 | Uncharacterized protein | NRLVQVVGGWLHSFAL | 0.43 | 1.5 | 0.65 | 6.69 | 155 |
| A0A0A2CWR1 | Uncharacterized protein | YKKVANYLREID | 0.65 | 1 | 0.65 | 4.29 | 156 |
| B4U1M3 | Uncharacterized protein | KVVKWVAGFFE | 0.65 | 1 | 0.65 | 5.99 | 157 |
| A0A0D1BIJ1 | Contig000026, whole genome shotgun sequence | KVVKWVAGFFE | 0.65 | 1 | 0.65 | 5.99 | 158 |
| A0A0D0Z7R1 | Contig000027, whole genome shotgun sequence | KVVKWVAGFFE | 0.65 | 1 | 0.65 | 5.99 | 159 |
| A0A0D1AR79 | Contig000095, whole genome shotgun sequence | KVVKWVAGFFE | 0.65 | 1 | 0.65 | 5.99 | 160 |
| C0MDI1 | Putative competence stimulating peptide | KVVKWVAGFFE | 0.65 | 1 | 0.65 | 5.99 | 161 |
| A0A0G2Z858 | Uncharacterized protein | GGGWIDGIKKIINL | 0.62 | 1 | 0.62 | 4.94 | 162 |
| L0G0E1 | Uncharacterized protein | AGIGAALFSSLIVTGGGMMSVGYSCGNKVKNGLRDY | 0.31 | 2 | 0.61 | 9.14 | 163 |
| A0A0B8T3S9 | Uncharacterized protein | GYEVGKSAAERARR | 0.30 | 2 | 0.61 | 5.23 | 164 |
| D5T3D9 | Uncharacterized protein | GGDVVKTLTRLFNQ | 0.60 | 1 | 0.60 | 4.86 | 165 |
| A0A0H3J316 | Uncharacterized protein | GGGIYDKINKFLSN | 0.58 | 1 | 0.58 | 4.19 | 166 |
| J3CI08 | Uncharacterized protein | LRTVTGGLEDCINPATGGCRKI | 0.57 | 1 | 0.57 | 9.56 | 167 |
| C1CCS2 | Conserved domain protein | AALGCAAGGVKYGKILGPWGAAIGGIGGAV | 0.29 | 2 | 0.57 | 5.89 | 168 |
| F8N6B2 | Uncharacterized protein | LGRGLGCGRGCGGC | 0.29 | 2 | 0.57 | 4.6 | 169 |
| Q729Z0 | Uncharacterized protein | GGVLRRCWRDWLDSFFAVQ | 0.57 | 1 | 0.57 | 11.25 | 170 |
| G6J8U1 | Putative membrane protein | AALGCAAGGVKYGRLLGPWGAAIGGIGGAV | 0.28 | 2 | 0.57 | 5.89 | 171 |
| C2EJ80 | Bacteriocin-type signal sequence | NFGKSYYGKCSF | 0.28 | 2 | 0.56 | 9.7 | 172 |
| A0A062WNU4 | Uncharacterized protein | GYIGGGNHLCKG | 0.37 | 1.5 | 0.56 | 5.08 | 173 |
| A0A064BZ31 | Uncharacterized protein | GYIGGGNHLCKG | 0.37 | 1.5 | 0.56 | 5.5 | 174 |
| A0A081QCP4 | Uncharacterized protein | GYIGGGNHLCKG | 0.37 | 1.5 | 0.56 | 5.48 | 175 |
| A0A0B7LYG0 | Uncharacterized protein | GYIGGGNHLCKG | 0.37 | 1.5 | 0.56 | 5.5 | 176 |
| A0A0E9GYM9 | Uncharacterized protein | GYIGGGNHLCKG | 0.37 | 1.5 | 0.56 | 5.11 | 177 |
| A5LKF7 | Uncharacterized protein | GYIGGGNHLCKG | 0.37 | 1.5 | 0.56 | 5.5 | 178 |
| A5M755 | Uncharacterized protein | GYIGGGNHLCKG | 0.37 | 1.5 | 0.56 | 5.5 | 179 |
| C1C6Q6 | Uncharacterized protein | GYIGGGNHLCKG | 0.37 | 1.5 | 0.56 | 5.5 | 180 |
| C1CDS2 | Uncharacterized protein | GYIGGGNHLCKG | 0.37 | 1.5 | 0.56 | 5.5 | 181 |
| D6ZLM5 | Uncharacterized protein | GYIGGGNHLCKG | 0.37 | 1.5 | 0.56 | 5.5 | 182 |
| E0Q149 | Uncharacterized protein | GYIGGGNHLCKG | 0.37 | 1.5 | 0.56 | 5.48 | 183 |
| G6LM33 | Uncharacterized protein | GYIGGGNHLCKG | 0.37 | 1.5 | 0.56 | 5.5 | 184 |
| M5K5U3 | Uncharacterized protein | GYIGGGNHLCKG | 0.37 | 1.5 | 0.56 | 5.5 | 185 |
| M5K8K8 | Uncharacterized protein | GYIGGGNHLCKG | 0.37 | 1.5 | 0.56 | 5.5 | 186 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| M5N786 | Uncharacterized protein | GYIGGGNHLCKG | 0.37 | 1.5 | 0.56 | 5.5 | 187 |
| Q8CYW4 | Uncharacterized protein | GYIGGGNHLCKG | 0.37 | 1.5 | 0.56 | 5.5 | 188 |
| S9RF90 | Uncharacterized protein | GYIGGGNHLCKG | 0.37 | 1.5 | 0.56 | 7.79 | 189 |
| V8IBA1 | Uncharacterized protein | GYIGGGNHLCKG | 0.37 | 1.5 | 0.56 | 5.48 | 190 |
| V8ID01 | Uncharacterized protein | GYIGGGNHLCKG | 0.37 | 1.5 | 0.56 | 5.48 | 191 |
| A0A0F7HB86 | Uncharacterized protein | GTSAVTVCRRVATC | 0.28 | 2 | 0.56 | 8.86 | 192 |
| U2NQ09 | Uncharacterized protein | GTSAVTVCRRVATC | 0.28 | 2 | 0.56 | 8.86 | 193 |
| B9DTX9 | Putative bacteriocin | GGLGGLQTGIKYCKV | 0.27 | 2 | 0.55 | 9.1 | 194 |
| A0A0D0Z195 | Contig000004, whole genome shotgun sequence | GAIGCASRGVKLGSRIGPWGAVIGGVGSAA | 0.18 | 3 | 0.54 | 7.71 | 195 |
| A0A0D1AE73 | Contig000013, whole genome shotgun sequence | GAIGCASRGVKLGSRIGPWGAVIGGVGSAA | 0.18 | 3 | 0.54 | 7.71 | 196 |
| A0A0D0ZZF1 | Contig000024, whole genome shotgun sequence | GAIGCASRGVKLGSRIGPWGAVIGGVGSAA | 0.18 | 3 | 0.54 | 7.71 | 197 |
| C0MH64 | Putative bacteriocin | GAIGCASRGVKLGSRIGPWGAVIGGVGSAA | 0.18 | 3 | 0.54 | 7.71 | 198 |
| C0CJI1 | Uncharacterized protein | MEKVSGGASRYQH | 0.36 | 1.5 | 0.54 | 9.99 | 199 |
| R5C531 | Uncharacterized protein | MEKVSGGASRYQH | 0.36 | 1.5 | 0.54 | 9.99 | 200 |
| R6VS52 | Uncharacterized protein | IDGYCSKCAEKIRNGQ | 0.54 | 1 | 0.54 | 8.37 | 201 |
| C1C5R3 | Conserved domain protein | AALGCAAGGVKYGRLLGLWGAAIGGIGGAV | 0.27 | 2 | 0.54 | 5.89 | 202 |
| A0A085HBT8 | Uncharacterized protein | TTLSQFFSKLFG | 0.54 | 1 | 0.54 | 4.39 | 203 |
| C5RBL9 | Uncharacterized protein | VKSLLGLLGGIMGM | 0.53 | 1 | 0.53 | 9.99 | 204 |
| M1WT49 | Uncharacterized protein | EILKGGKTLVTPL | 0.53 | 1 | 0.53 | 9.96 | 205 |
| W0BBY2 | Uncharacterized protein | LSKVSGGASQMTH | 0.35 | 1.5 | 0.52 | 4.45 | 206 |
| Q5FI68 | Uncharacterized protein | GSGRGGGAQMRAIGS | 0.26 | 2 | 0.52 | 11.62 | 207 |
| R6R6T2 | Uncharacterized protein | TLFNYIARVFSAGSSIINN | 0.52 | 1 | 0.52 | 5.14 | 208 |
| A0A0H2UPL5 | Uncharacterized protein | SGYIGGGNHLCKG | 0.35 | 1.5 | 0.52 | 5.5 | 209 |
| K9RTP0 | Uncharacterized protein | QLTGGFRSYGRQLDG | 0.52 | 1 | 0.52 | 4.61 | 210 |
| R2M4F0 | Uncharacterized protein | TAKQCLQAIGSWG | 0.52 | 1 | 0.52 | 5.98 | 211 |
| R7ICH1 | Uncharacterized protein | ASFFNSVARILRTAYDIG | 0.52 | 1 | 0.52 | 9.85 | 212 |
| R7HKI2 | Uncharacterized protein | SMLTAIYKTLEVIYQIGESLGNYIRR | 0.51 | 1 | 0.51 | 6.15 | 213 |
| Q38Y63 | Hypothetical small peptide | GLGKLVRAGVDIG | 0.51 | 1 | 0.51 | 9.99 | 214 |
| Q6KCF2 | Putative beta-peptide | GLGKLVRAGVDIG | 0.51 | 1 | 0.51 | 9.99 | 215 |
| W4QHA2 | Uncharacterized protein | LLGLCTGFYGVYKTV | 0.50 | 1 | 0.50 | 9.65 | 216 |
| H2AM33 | Uncharacterized protein | AGLGNGLKQWNT | 0.49 | 1 | 0.49 | 6.53 | 217 |
| H1WT90 | Uncharacterized protein | VVSFGKGIVSAFG | 0.49 | 1 | 0.49 | 9.87 | 218 |
| R6N077 | Uncharacterized protein | ATMMNAIYKTIEIIFNIGEAFGSYIRR | 0.49 | 1 | 0.49 | 6.15 | 219 |
| A0A086AYC6 | Uncharacterized protein | GECRKYGRGCAEQ | 0.48 | 1 | 0.48 | 9.3 | 220 |
| R7M280 | Uncharacterized protein | MINALTKAVTALYDLGKGFGSA | 0.48 | 1 | 0.48 | 8.98 | 221 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| R5HCU1 | Uncharacterized protein | ASFLNAISRGIETFLNLGRM | 0.48 | 1 | 0.48 | 9.78 | 222 |
| F4AFZ5 | Uncharacterized protein | VLSAASGAGTGIKACKSFG | 0.24 | 2 | 0.48 | 9.14 | 223 |
| W4QQL4 | Uncharacterized protein | LFGLATGFYGVYRAI | 0.48 | 1 | 0.48 | 9.87 | 224 |
| I9T9Y4 | Uncharacterized protein | YEKINGVLTRVFTFS | 0.47 | 1 | 0.47 | 7.9 | 225 |
| A0A0F3H1F2 | Uncharacterized protein | ATVNTVVNGWMRYG | 0.47 | 1 | 0.47 | 9.18 | 226 |
| T0TP63 | Uncharacterized protein | ATVNTVVNGWMRYG | 0.47 | 1 | 0.47 | 9.18 | 227 |
| E3CS41 | Uncharacterized protein | ATVNTVVNGWMKYG | 0.47 | 1 | 0.47 | 9.14 | 228 |
| J8IIA4 | Uncharacterized protein | RIVTALSAFFTSGFTVL | 0.47 | 1 | 0.47 | 9.63 | 229 |
| A0A0F2DG91 | Uncharacterized protein | MGQGALNSYRDAWK | 0.46 | 1 | 0.46 | 4.61 | 230 |
| E1LEJ5 | Uncharacterized protein | MGQGALNSYRDAWK | 0.46 | 1 | 0.46 | 4.61 | 231 |
| C0BVX0 | Uncharacterized protein | EVKKLFQDAANSAMK | 0.46 | 1 | 0.46 | 6.03 | 232 |
| T1ZF04 | Uncharacterized protein | AKSGIAGGAGNGLRLG | 0.23 | 2 | 0.46 | 8.77 | 233 |
| L0KBX6 | Uncharacterized protein | KAMVKDGWKLIETA | 0.46 | 1 | 0.46 | 4.07 | 234 |
| A0A0D5BQU9 | Uncharacterized protein | GKLRAWGGGCDS | 0.45 | 1 | 0.45 | 9.34 | 235 |
| F9HJW5 | Uncharacterized protein | WGVFKSVIGTFGP | 0.45 | 1 | 0.45 | 4.96 | 236 |
| A0A086AWR6 | Uncharacterized protein | CANGVCRPIAGAG | 0.45 | 1 | 0.45 | 8.86 | 237 |
| Q8FUD5 | Uncharacterized protein | GGGGIARELATMLRP | 0.44 | 1 | 0.44 | 11.6 | 238 |
| I0GCL8 | Uncharacterized protein | HDGLKVAEAIIKAITH | 0.44 | 1 | 0.44 | 5.13 | 239 |
| C2LRN7 | Uncharacterized protein | NGGGILSSVAGLVKDTWGTLYSTGRDFGRSVVN | 0.43 | 1 | 0.43 | 4.44 | 240 |
| E0S535 | Uncharacterized protein | KYYTAICATYQAALDLCARVG | 0.42 | 1 | 0.42 | 6.08 | 241 |
| A0A077EAB3 | Uncharacterized protein | MAQLKGGIKSVEG | 0.42 | 1 | 0.42 | 9.05 | 242 |
| R7P6R1 | Uncharacterized protein | IIGAISGYINPVKC | 0.41 | 1 | 0.41 | 9.04 | 243 |
| K2DVP9 | Uncharacterized protein | KTADQVAREAGAAGREIK | 0.41 | 1 | 0.41 | 9.05 | 244 |
| A0A0F2E6T0 | Excreted peptide | STICTRMTGYGNGII | 0.41 | 1 | 0.41 | 3.62 | 245 |
| S9SM70 | Excreted peptide | STICTRMTGYGNGII | 0.41 | 1 | 0.41 | 3.62 | 246 |
| A0A023BZ22 | Uncharacterized protein | VLAAIGGLYKAGEAIGKG | 0.41 | 1 | 0.41 | 5.05 | 247 |
| A0A077ECN9 | Uncharacterized protein | MAQLKGGMQEIAKTCAAGS | 0.40 | 1 | 0.40 | 9.07 | 248 |
| A0A077EE44 | Uncharacterized protein | MAQLKGGMQEIAKTCAAGS | 0.40 | 1 | 0.40 | 9.07 | 249 |
| U2CMK8 | Uncharacterized protein | KVKQFFEQGAKSAME | 0.40 | 1 | 0.40 | 6.04 | 250 |
| F8LL37 | Uncharacterized conserved protein | VATGVGNGLRLGIKTRTWQGAVAGAAGGAIVGGVGY | 0.13 | 3 | 0.40 | 6.01 | 251 |
| F8HFT9 | Pore-forming peptide, putative bacteriocin | VATGVGNGLRLGIKTRTWQGAVAGAAGGAIVGGVGY | 0.13 | 3 | 0.40 | 6.01 | 252 |
| F8LRT1 | Pore-forming peptide, putative bacteriocin | VATGVGNGLRLGIKTRTWQGAVAGAAGGAIVGGVGY | 0.13 | 3 | 0.40 | 6.01 | 253 |
| Q5M2W2 | Pore-forming peptide, putative bacteriocin | VATGVGNGLRLGIKTRTWQGAVAGAAGGAIVGGVGY | 0.13 | 3 | 0.40 | 6.01 | 254 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| A0A086B2P4 | Uncharacterized protein | LKTIKGGGDQGV | 0.39 | 1 | 0.39 | 9.27 | 255 |
| M4YVZ4 | Hypothetical membrane associated protein | IIGGLGGLASGLKF | 0.38 | 1 | 0.38 | 5.46 | 256 |
| A0A0E2IVJ2 | Uncharacterized protein | IAGGAGNGLRLGIKTRTWQGVVAGAVGGAIIGGVGY | 0.13 | 3 | 0.38 | 8.77 | 257 |
| I0S9I1 | Uncharacterized protein | IAGGAGNGLRLGIKTRTWQGVVAGAVGGAIIGGVGY | 0.13 | 3 | 0.38 | 8.77 | 258 |
| A0A087QC98 | Uncharacterized protein | GGKAVNGFVNGN | 0.37 | 1 | 0.37 | 6.17 | 259 |
| D1YGH0 | Uncharacterized protein | GGKAVNGFVNGN | 0.37 | 1 | 0.37 | 6.17 | 260 |
| A0A077EA21 | Uncharacterized protein | MAQLKGGIKNADG | 0.37 | 1 | 0.37 | 9.05 | 261 |
| A0A077EFY9 | Uncharacterized protein | MAQLKGGIKNADG | 0.37 | 1 | 0.37 | 9.05 | 262 |
| A0A086A6U3 | Uncharacterized protein | RACTLISSGCAQ | 0.37 | 1 | 0.37 | 8.59 | 263 |
| F8NCK2 | Uncharacterized protein | QKGMSQVRGGVQE | 0.37 | 1 | 0.37 | 5.28 | 264 |
| A0A0F2CQG4 | Uncharacterized protein | SIWKVGGAVVGGATALFA | 0.37 | 1 | 0.37 | 4.2 | 265 |
| A0A0H0YQB5 | Uncharacterized protein | GLGAIARSWAQGGF | 0.35 | 1 | 0.35 | 5.04 | 266 |
| A0A0H0YSB4 | Uncharacterized protein | GLGAIARSWAQGGF | 0.35 | 1 | 0.35 | 5 | 267 |
| K9E1K0 | Uncharacterized protein | CAKSGNAAGAAVMSAH | 0.23 | 1.5 | 0.35 | 8.43 | 268 |
| J3CSM9 | Uncharacterized protein | VRALLGGIIATGSA | 0.35 | 1 | 0.35 | 11.65 | 269 |
| A0A0H2UTD9 | Uncharacterized protein | VIGGLGGLASGLKF | 0.34 | 1 | 0.34 | 6.5 | 270 |
| Q9A137 | Uncharacterized protein | VIGGLGGLASGLKF | 0.34 | 1 | 0.34 | 6.5 | 271 |
| C5WF58 | Hypothetical membrane associated protein | VIGGLGGLASGLKF | 0.34 | 1 | 0.34 | 6.5 | 272 |
| Q1J801 | Hypothetical membrane associated protein | VIGGLGGLASGLKF | 0.34 | 1 | 0.34 | 6.5 | 273 |
| Q1JI59 | Hypothetical membrane associated protein | VIGGLGGLASGLKF | 0.34 | 1 | 0.34 | 6.5 | 274 |
| Q1JN16 | Hypothetical membrane associated protein | VIGGLGGLASGLKF | 0.34 | 1 | 0.34 | 6.5 | 275 |
| Q48UV8 | Hypothetical membrane associated protein | VIGGLGGLASGLKF | 0.34 | 1 | 0.34 | 6.5 | 276 |
| Q5XDF5 | Hypothetical membrane associated protein | VIGGLGGLASGLKF | 0.34 | 1 | 0.34 | 6.5 | 277 |
| I7J3B0 | Uncharacterized protein | DFWHKLMDSLCRNFNS | 0.68 | 0.5 | 0.34 | 6.54 | 278 |
| F5ZAJ3 | Uncharacterized protein | RGGGWVGAAIGAISGGLG | 0.34 | 1 | 0.34 | 4.4 | 279 |
| G0IAJ6 | Uncharacterized protein | SIWKIGAAVAGGAAALFA | 0.34 | 1 | 0.34 | 4.2 | 280 |
| K0ZN36 | Uncharacterized protein | AAKIAGGITAAG | 0.34 | 1 | 0.34 | 4.08 | 281 |
| K1A1E3 | Uncharacterized protein | AAKIAGGITAAG | 0.34 | 1 | 0.34 | 4.08 | 282 |
| A0A0F3HMF2 | Uncharacterized protein | SIWKVGAAVAGGATALFA | 0.33 | 1 | 0.33 | 4.25 | 283 |
| X8FLG5 | Uncharacterized protein | AAGWKACSSIYGM | 0.33 | 1 | 0.33 | 5.49 | 284 |
| A0A0H8RN19 | Putative transporter | LVSGGIALGSRCG | 0.32 | 1 | 0.32 | 4.89 | 285 |
| A0A0J7IN65 | Uncharacterized protein | TGPKYCSTYIGC | 0.32 | 1 | 0.32 | 9.04 | 286 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| S6C1D9 | Uncharacterized protein | GLGAIARSWAQGGFA | 0.32 | 1 | 0.32 | 5.04 | 287 |
| A5M594 | Uncharacterized protein | KAIAGGTALIGSGWAAG | 0.31 | 1 | 0.31 | 3.57 | 288 |
| U2EXV9 | Uncharacterized protein | TFGGGGDAAAAGVRK | 0.31 | 1 | 0.31 | 7.89 | 289 |
| A5LJ32 | Uncharacterized protein | KVIAGGTALIGSGLAAG | 0.30 | 1 | 0.30 | 3.57 | 290 |
| A0A0B7LKX0 | Excreted peptide | KVIAGGTALIGSGLAAG | 0.30 | 1 | 0.30 | 3.57 | 291 |
| Q6SZ94 | Bacteriocin-type signal sequence-containing protein (MundKS) (Mundticin) | NSAANLATGGAAGWKS | 0.29 | 1 | 0.29 | 9.7 | 292 |
| A0RJ68 | Uncharacterized protein | AGVAGFTKVAGAITAGAG | 0.29 | 1 | 0.29 | 9.52 | 293 |
| B3Z892 | Uncharacterized protein | AGVAGFTKVAGAITAGAG | 0.29 | 1 | 0.29 | 9.52 | 294 |
| C2UP09 | Uncharacterized protein | AGVAGFTKVAGAITAGAG | 0.29 | 1 | 0.29 | 9.7 | 295 |
| A0A0H2UN03 | Uncharacterized protein | KAIAGGTALIGSGLAAG | 0.29 | 1 | 0.29 | 3.57 | 296 |
| A0A0H2ZQ92 | Uncharacterized protein | KAIAGGTALIGSGLAAG | 0.29 | 1 | 0.29 | 3.57 | 297 |
| B1I840 | Uncharacterized protein | KAIAGGTALIGSGLAAG | 0.29 | 1 | 0.29 | 3.57 | 298 |
| B2IRL0 | Uncharacterized protein | KAIAGGTALIGSGLAAG | 0.29 | 1 | 0.29 | 3.57 | 299 |
| C1CAF3 | Uncharacterized protein | KAIAGGTALIGSGLAAG | 0.29 | 1 | 0.29 | 3.57 | 300 |
| C1CBU7 | Uncharacterized protein | KAIAGGTALIGSGLAAG | 0.29 | 1 | 0.29 | 3.57 | 301 |
| G0IBD6 | Uncharacterized protein | KAIAGGTALIGSGLAAG | 0.29 | 1 | 0.29 | 3.57 | 302 |
| J1DKQ8 | Uncharacterized protein | KAIAGGTALIGSGLAAG | 0.29 | 1 | 0.29 | 3.57 | 303 |
| Q8CZA0 | Uncharacterized protein | KAIAGGTALIGSGLAAG | 0.29 | 1 | 0.29 | 3.57 | 304 |
| R0N8A8 | Uncharacterized protein | KAIAGGTALIGSGLAAG | 0.29 | 1 | 0.29 | 3.57 | 305 |
| A0A0C1QXM7 | Uncharacterized protein | VLKSMNAVASAFQFIAL | 0.28 | 1 | 0.28 | 4.13 | 306 |
| A0A069P4B0 | Uncharacterized protein | AGGRAVSAIVDGR | 0.28 | 1 | 0.28 | 5.03 | 307 |
| B1BHK0 | Uncharacterized protein | KAVALISAGVTTLAGAAA | 0.28 | 1 | 0.28 | 4.78 | 308 |
| B1BU21 | Uncharacterized protein | KAVALISAGVTTLAGAAA | 0.28 | 1 | 0.28 | 4.78 | 309 |
| B1RC11 | Uncharacterized protein | KAVALISAGVTTLAGAAA | 0.28 | 1 | 0.28 | 4.78 | 310 |
| I7H0S7 | Uncharacterized protein | KAVALISAGVTTLAGAAA | 0.28 | 1 | 0.28 | 4.78 | 311 |
| A0A0D7QJF4 | Uncharacterized protein | LAGKALDALSHATDHTPTNVLNGMLGAIGR | 0.28 | 1 | 0.28 | 4.97 | 312 |
| R7AVY5 | Uncharacterized protein | MKEYAQSASDAKVKQFFEKGAKSA | 0.14 | 2 | 0.27 | 7.88 | 313 |
| A0A0D1B9N5 | Contig000008, whole genome shotgun sequence | SHLPSIFEKFCNWIGM | 0.54 | 0.5 | 0.27 | 9.89 | 314 |
| B1BHJ9 | Uncharacterized protein | TGAAIAKGAAAIGTA | 0.26 | 1 | 0.26 | 6.53 | 315 |
| B1BU20 | Uncharacterized protein | TGAAIAKGAAAIGTA | 0.26 | 1 | 0.26 | 6.53 | 316 |
| B1RC12 | Uncharacterized protein | TGAAIAKGAAAIGTA | 0.26 | 1 | 0.26 | 6.53 | 317 |
| I7H937 | Putative bacteriocin | TGAAIAKGAAAIGTA | 0.26 | 1 | 0.26 | 6.53 | 318 |
| E3CPS2 | Uncharacterized protein | HTVYDFGRGFVDGFRG | 0.51 | 0.5 | 0.26 | 6.51 | 319 |
| E8KT24 | Uncharacterized protein | HTVYDFGRGFVDGFRG | 0.51 | 0.5 | 0.26 | 6.51 | 320 |
| T0TQ78 | Uncharacterized protein | HTVYDFGRGFVDGFRG | 0.51 | 0.5 | 0.26 | 8.12 | 321 |

TABLE 3-continued

Representative peptides identifies from the primary screen

| Accession # | Name | Comp Form Match | HM | Q | HMQ | PI | SEQ ID NO: |
|---|---|---|---|---|---|---|---|
| X8JP08 | Uncharacterized protein | HTVYDFGRGFVDGFRG | 0.51 | 0.5 | 0.26 | 8.12 | 322 |
| E1M7J2 | Uncharacterized protein | KAIAGGTALVGSGLTAG | 0.26 | 1 | 0.26 | 3.71 | 323 |
| D6E340 | Uncharacterized protein | FWTLVAAGFAGGIATGVSR | 0.25 | 1 | 0.25 | 8.14 | 324 |
| A0A0F2CYI7 | Uncharacterized protein | KAIAGGTALVGSGLAAG | 0.25 | 1 | 0.25 | 3.66 | 325 |
| A0A0F2DGV3 | Uncharacterized protein | KAIAGGTALVGSGLAAG | 0.25 | 1 | 0.25 | 3.5 | 326 |
| A0A0F3HMX5 | Uncharacterized protein | KAIAGGTALVGSGLAAG | 0.25 | 1 | 0.25 | 3.71 | 327 |

Class II bacteriocins are typically small, cationic peptides that often contain a conserved leader peptide sequence that is important for downstream processing of the mature peptide. This leader peptide is characterized as having a highly conserved double-glycine motif that has been shown to be essential for proper cleavage of the bacteriocin precursor. Beyond this motif, a number of other residues within the leader sequence are also conserved to varying degrees.

Within the field, it has been assumed that the conservation of these residues was likely due to a specificity of the enzyme that carried out cleavage of the signal peptide domain. This supposition has recently been borne out with the structural characterization of a prototypic ABC transporter, demonstrating that only very small residues, such as glycine, can be accommodated in the cleft containing the active site of this protease. This example also suggested that the enzyme would have strong preferences for specific polar or non-polar residues along the signal peptide template.

In the present study, an alignment of more than 200 prototypic class II bacteriocins was carried out to generate a more relaxed signal peptide consensus sequence. In particular, in addition to the C-terminal double glycine motif, this consensus allowed for any polar residue at positions −9 and −11 of the signal peptide backbone. Moreover, an expanded set of hydrophobic residues was allowed at positions −4 and −7, to generate a consensus that may be more representative of a broad number of known bacteriocin sequences.

Once complete, this expanded consensus was used as an initial step within a multi-component search method to probe for new bacteriocin sequences in genomic data templates. This retrieved a large percentage (88-90%) of the currently known class IIa and IIb linear bacteriocins. Hence, the application of this multi-component search method may provide a useful way to rapidly screen new sequence data for the presence of bacteriocin sequences. Such methods may serve as an adjunct to currently used computational gene identification tools as many small peptides are not correctly identified or annotated in current genome sequencing projects.

Beyond the signal peptide consensus screen, a second component of the search method made use of a newly identified amphipathic search formula to probe for α-helical domains within the retrieved peptide dataset. The tests using this formula have demonstrated that it is highly accurate, identifying alpha-helical domains with greater than 90% efficiency. Application of the amphipathic search formula returned virtually all of the bacteriocins identified in the primary signal peptide-based screen with the exception of the pediocin peptides.

Residue Frequency

Abundance of Glycine and Alanine

Figure 5:
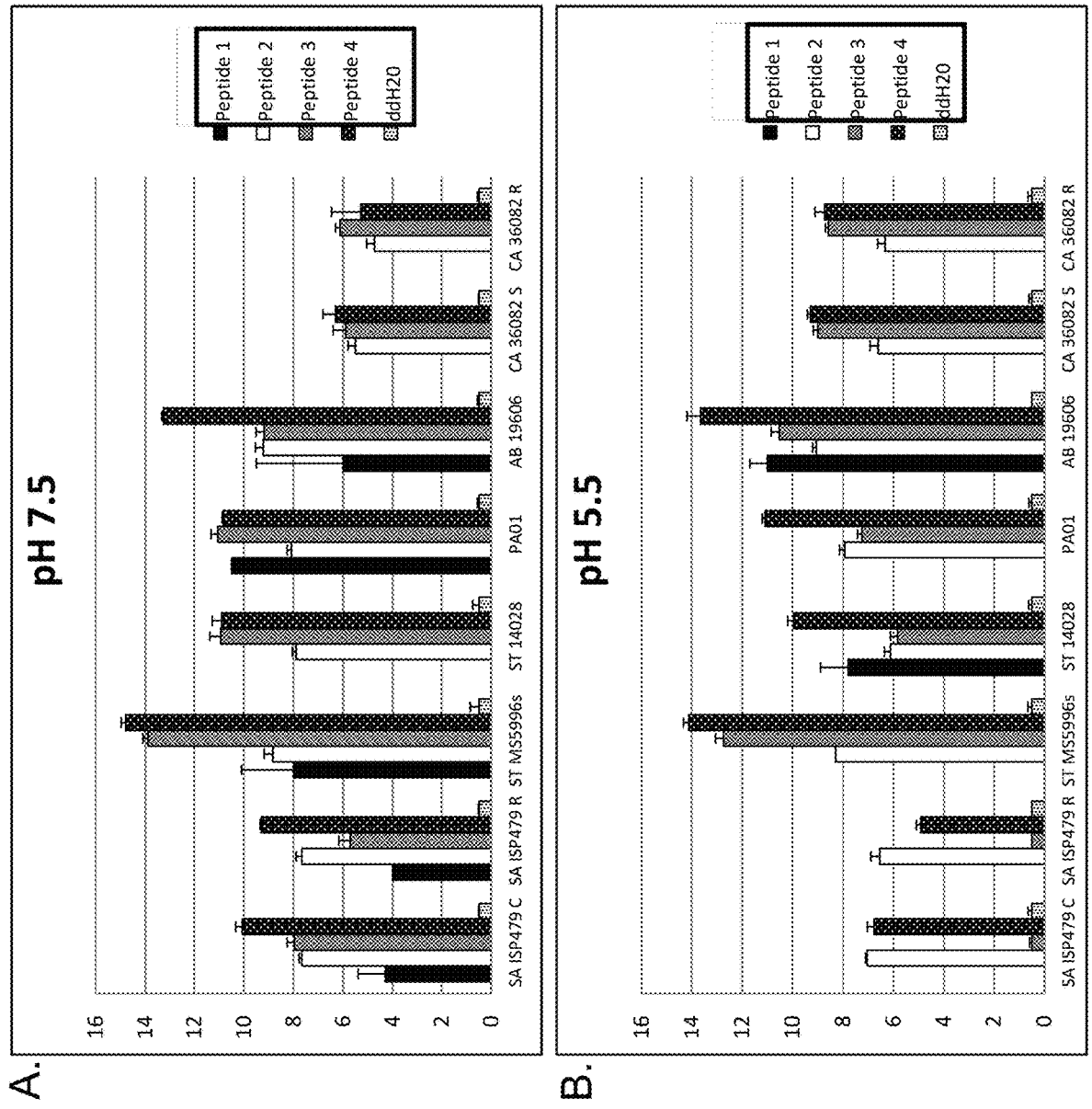
FIG. 5, with panels A and B, shows the antimicrobial activity of putative bacteriocins. Microbicidal activity of study test peptides versus a panel of prototypic gram-positive (*S. aureus*), gram-negative (*S. typhimurium, P. aeruginosa, A. baumannii*) and fungal (*C. albicans*) pathogens at two pH's representing: A—native physiologic (pH 7.5); or B—phagolysosomal (pH 5.5) environments.

As the amphipathic search formula returns aligned datasets, it was possible to determine the frequency of individual residues on both the polar and non-polar faces of a predicted 18 residue α-helical span of returned peptides. One outcome of this analysis was the finding that glycine was the most abundant residue at nearly all positions of the polar face of the peptide and, if not the most abundant, then highly represented on the non-polar face of the returned sequences (FIG. 5). It is also of interest that after glycine one of the second most abundant residues at all positions on both peptide faces was alanine.

These findings lend support to one of the reigning theories regarding the mechanism by which many α-helical antimicrobial peptides are presumed to limit self-toxicity prior to interacting with their intended target. This theory proposes that an abundance of small, sterically-unrestrained residues with a high degree of rotational freedom, such as glycine and alanine, serve to keep α-helical antimicrobial peptides in an unstructured and non-toxic conformation in aqueous environments. Such peptides only then become organized to adopt their microbicidal amphipathic structure when they encounter the hydrophobic milieu of the target membrane. Support for this theory is provided by: 1) the finding of an abundance of glycine, and to a lesser extent alanine, residues in the α-helical antimicrobial peptides of many organisms; and 2) a significant number of structural studies which demonstrate that many a-helical antimicrobial peptides are unstructured in aqueous solutions only to adopt an α-helical conformation in the presence of membrane mimetic environments.

In the current example, the finding of an abundance of glycine and alanine in the retrieved bacteriocins would suggest that these peptides may also utilize a similar mechanism to limit self-toxicity.

Preference of Lysine over Arginine

One additional mechanism by which a-helical antimicrobial peptides are thought to exert their microbicidal effect, is via a relative abundance of cationic residues which are thought to enhance their selectivity towards anionic surface lipids and the increased electronegative potential of many bacterial species. In the present study, a large proportion of the retrieved sequences were cationic in nature, an observation that supports this hypothesis. One additional finding was a strong preference for an abundance of lysine over arginine in the retrieved bacteriocin sequences. While the significance of this observation is not known, it is in alignment with a similar preference for lysine over arginine in many α-helical antimicrobial peptides of eukaryotes. Biophysical studies have found that lysine is less efficient at generating negative Gaussian membrane curvature, and pore-like structures, than arginine. However, many α-helical antimicrobial peptides have an increased net hydrophobicity, as compared with other more arginine-rich classes of antimicrobial proteins, a feature that may compensate for this reduced permeabilizing efficiency.

Spectrum/Potency

Sequences retrieved by the multi-component sequence formula were screened for a number of biophysical parameters, and based on these findings, and their localization to bacteriocin-like operons, four putative bacteriocin peptides were synthesized and assessed for microbicidal activity. Notably, all four peptides were found to have activity against a broad spectrum of microorganisms, with particular potency against a number of Gram negative pathogens. While historically it was reported that bacteriocin peptides were relatively narrow spectrum antibiotics, being most potent against closely related Gram positive organisms, more recent studies have found that in fact many bacteriocins have a much broader spectrum with microbicidal activity towards Gram negative and fungal organisms as well. These more recent studies reflect what was found in this report where all four putative bacteriocin peptides had activity against Gram positive, Gram negative and fungal organisms.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

SEQUENCE LISTING

The patent contains a lengthy sequence listing. A copy of the sequence listing is available in electronic form from the USPTO web site (https://seqdata.uspto.gov/?pageRequest=docDetail&DocID=US12037368B2). An electronic copy of the sequence listing will also be available from the USPTO upon request and payment of the fee set forth in 37 CFR 1.19(b)(3).

The invention claimed is:

1. A method of treating an infection in a patient in need thereof, comprising administering to the patient an effective amount of an isolated peptide, wherein the peptide is not longer than 45 amino acid residues in length and comprises the amino acid sequence of SEQ ID NO: 9.

2. The method of claim 1, wherein the infection is caused by a Gram-negative bacterium, a Gram-positive bacterium or a fungus.

3. The method of claim 1, wherein the peptide is not longer than 40 amino acid residues in length.

4. The method of claim 3, wherein the peptide is not longer than 35 amino acid residues in length.

* * * * *